US012734268B2

(12) United States Patent
Wang et al.

(10) Patent No.: US 12,734,268 B2
(45) Date of Patent: Sep. 15, 2026

(54) EXPANDABLE HEMOSTATIC TABLETS COMPRISING OXIDIZED REGENERATED CELLULOSE

(71) Applicant: Ethicon, Inc., Raritan, NJ (US)

(72) Inventors: Yi-Lan Wang, Belle Mead, NJ (US); Tien-Jung Lee, Basking Ridge, NJ (US)

(73) Assignee: Ethicon, Inc., Raritan, NJ (US)

( * ) Notice: Subject to any disclaimer, the term of this patent is extended or adjusted under 35 U.S.C. 154(b) by 758 days.

(21) Appl. No.: 18/053,628

(22) Filed: Nov. 8, 2022

(65) Prior Publication Data

US 2024/0148933 A1 May 9, 2024

(51) Int. Cl.
*A61L 15/28* (2006.01)

(52) U.S. Cl.
CPC ........... *A61L 15/28* (2013.01); *A61L 2400/04* (2013.01)

(58) Field of Classification Search
CPC ....................................................... A61L 15/28
See application file for complete search history.

(56) References Cited

U.S. PATENT DOCUMENTS 3,364,200 A 1/1968 Ashton et al.
5,180,398 A 1/1993 Boardman et al.
5,823,983 A 10/1998 Rosofsky
8,518,064 B2 8/2013 Kurrus et al.
8,815,832 B2 8/2014 Wang
8,828,050 B2 9/2014 Gregory et al.
10,034,957 B2 7/2018 Wang
11,007,301 B2 5/2021 Ilan et al.
2005/0287215 A1 12/2005 Looney et al.
2006/0078589 A1 4/2006 Jensen et al.
2007/0014862 A1 1/2007 Pameijer
2008/0027365 A1 1/2008 Huey
2010/0184968 A1 7/2010 Bertholon et al.
2012/0101520 A1 4/2012 Ginn et al.
2014/0142523 A1 5/2014 Steinbaugh et al.
2016/0250013 A1 9/2016 Skalla et al.
2019/0209389 A1* 7/2019 Jacobs .................. A61F 15/002
2021/0038757 A1* 2/2021 Ilan .......................... A61L 15/42
2021/0379237 A1* 12/2021 Veruva .................... A61L 15/64

OTHER PUBLICATIONS

International Search report issued for co-pending PCT application No. PCT/IB2023/061109, Mailing date of International Search report: Jan. 31, 2024.
Written Opinion issued for co-pending PCT application No. PCT/IB2023/061109, Mailing date of Written Opinion: Jan. 31, 2024.

* cited by examiner

*Primary Examiner* — Susan T Tran
*Assistant Examiner* — William Craigo
(74) *Attorney, Agent, or Firm* — David R. Crichton; Leo B. Kriksunov

(57) ABSTRACT

The present invention is directed to compressed hemostatic tablets or forms comprising a fibrous non-woven oxidized cellulose (OC or ORC) multilayer material compressed into a form stable tablet, further comprising calcium salt, with the tablets rapidly expandable on contact with blood or blood plasma. The compressed forms may further comprise a multi-arm PEG-SG and are dimensionally, preferably with regard to length and width, stable for at least 48 hours after compression. In some embodiments, the compressed forms will expand upon contact with blood from 1.5 to 5 times of tablet length in 5 seconds; from 2 to 6 times of tablet length in 20 seconds; and from 3 to 6 times of tablet length in 5 minutes. The compressed forms are effective in hemostasis in heparinized blood.

11 Claims, 22 Drawing Sheets

Compressed Fibrillar

Compressed SNoW

Compressed Fibrillar

Compressed SNoW

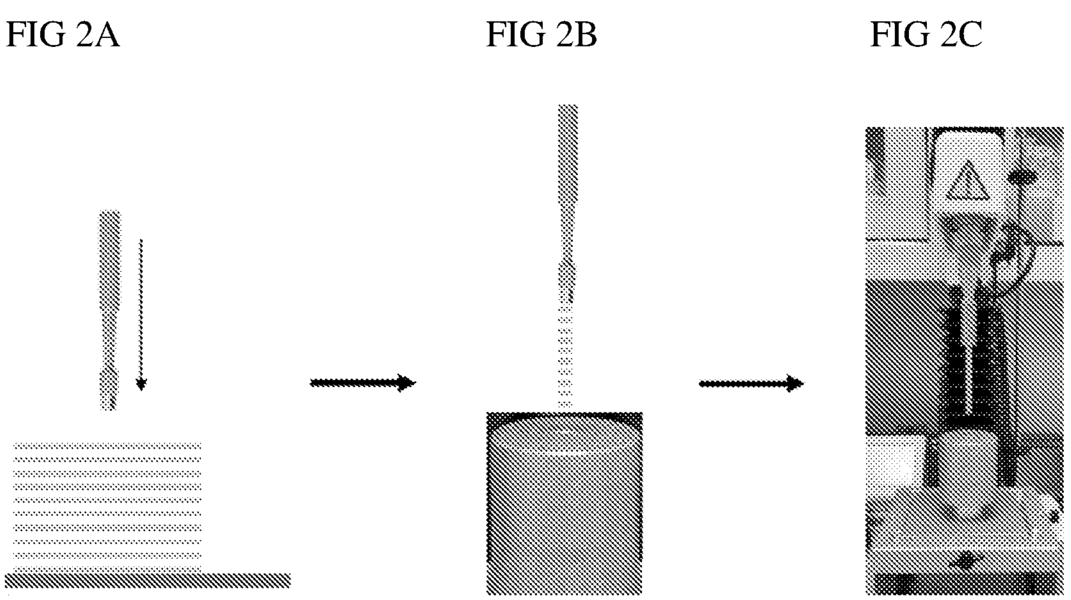
FIG 2A
FIG 2B
FIG 2C
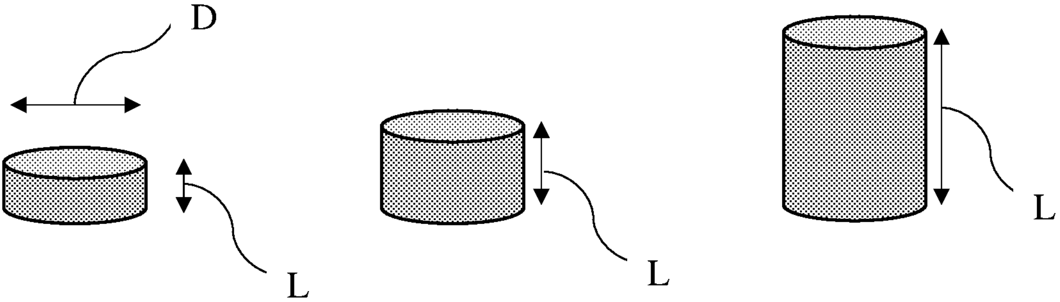
FIG 2D
FIG 2E
FIG 2F
D
L
L
L

Thickness: 3mm
Thickness: 5mm
Thickness: 10mm
Plastic deformation
Elastic deformation
Force (g)
20000
18000
16000
14000
12000
10000
8000
6000
4000
2000
0
-2000
0
2
4
6
8
10
12
Time (sec)

Figure 11A:
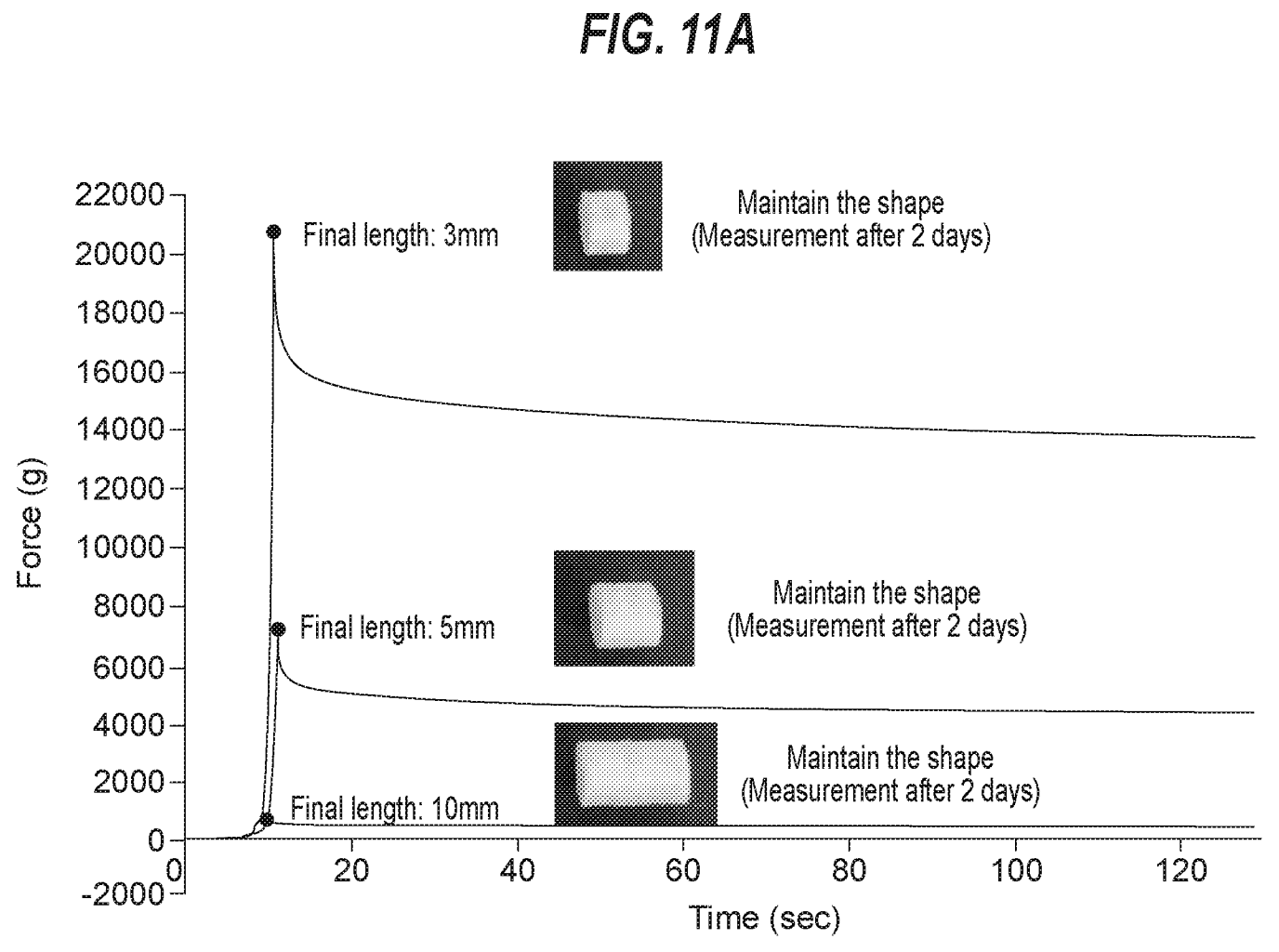

Final length: 3mm
Maintain the shape
(Measurement after 2 days)
Final length: 5mm
Maintain the shape
(Measurement after 2 days)
Final length: 10mm
Maintain the shape
(Measurement after 2 days)

Force (g)
22000
20000
18000
16000
14000
12000
10000
8000
6000
4000
2000
0
-2000

0
20
40
60
80
100
120
Time (sec)

10 % CaCl2
10 % CaCl2
10 % CaCl2

20 % CaCl2
20 % CaCl2
20 % CaCl2

EXPANDABLE HEMOSTATIC TABLETS COMPRISING OXIDIZED REGENERATED CELLULOSE

FIELD OF THE INVENTION

The present invention generally relates to expandable biodegradable hemostatic forms or tablets made of oxidized cellulose (OC) or oxidized regenerated cellulose (ORC) and various additives improving performance of the compressed tablets for treating a wound.

BACKGROUND OF THE INVENTION

In a wide variety of circumstances, animals, including humans, can suffer from bleeding due to wounds or during surgical procedures. In some circumstances, the bleeding is relatively minor and normal blood clotting functions, so the application of simple first aid is all that is required. In other circumstances substantial bleeding can occur. These situations usually require specialized equipment and materials as well as personnel trained to administer appropriate aid.

Conventional methods to achieve hemostasis include the use of surgical techniques, sutures, ligatures or clips, and energy-based coagulation or cauterization. When these conventional measures are ineffective or impractical, adjunctive hemostasis techniques and products are required.

The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

In an effort to address the above-described problems, materials have been developed for controlling excessive bleeding. Topical Absorbable Hemostats (TAHs) are widely used in surgical applications. TAHs encompass products based on oxidized cellulose (OC), gelatin, collagen, chitin, chitosan, etc. To improve the hemostatic performance, scaffolds based on the above materials can be combined with biologically-derived clotting factors, such as thrombin and fibrinogen.

Due to its biodegradability, and its bactericidal and hemostatic properties, oxidized cellulose (OC)-based materials, such as oxidized regenerated cellulose (ORC), have long been used as topical hemostats in a variety of surgical procedures, including neurosurgery, abdominal surgery, cardiovascular surgery, thoracic surgery, head and neck surgery, pelvic surgery and skin and subcutaneous tissue procedures. Several methods for forming various types of hemostats based on ORC materials are known, whether made in powder, woven, non-woven, knit, and other forms.

U.S. Patent Application having Publication No. 2012/0101520 relates to apparatus and methods used to seal a vascular puncture site, particularly sites of punctures that are the result of catheterization or other interventional procedures. The sealing device includes a sealing member and a tether. The sealing member occupies a space in an incision, puncture, or other wound and sealing the space that it occupies, to prevent further blood flow. The tether is attached to the sealing member, and provides the user with the ability to withdraw the sealing member if necessary.

U.S. Pat. No. 8,518,064 relates generally to a method for anchoring an expandable biocompatible plug material to a vessel wall to form an anchored occluding plug blocking or reducing blood flow to a desired vessel target, such as an artery supplying blood to a neoplastic tissue or tumor.

U.S. Patent Application having Publication No. 2005/0287215 discloses a plurality of packed particles that contain interstitial pores, where the interstitial pores have a pore volume and a median pore diameter effective to provide improved absorption of physiological fluids or an aqueous media when placed in contact therewith, compared to a plurality of unpacked particles of the same material, where the particles are made of a biocompatible material and have an average diameter suitable for use in providing hemostasis to a site of a body of a mammal requiring hemostasis, hemostatic compositions containing such plurality of packed particles, methods of making such particles and compositions and medical devices suitable for delivering and containing the hemostatic plurality of particles and/or composition to a site of a body.

U.S. Patent Application having Publication No. 2014/0142523 discloses, self-expanding wound dressings that include a first outer layer, a second outer layer, and a liquid-expandable layer disposed between the first outer layer and the second outer layer, wherein the liquid-expandable layer includes a plurality of liquid-expandable articles retained by a substrate, wherein the plurality of liquid-expandable articles expand to form expanded articles upon contact with a liquid.

U.S. Pat. No. 8,828,050 relates to hemostatic composition comprising a plurality of liquid expandable articles capable of expanding upon contact with a liquid. A suitable composition comprises a plurality of liquid-expandable articles that may be mechanically uncoupled from one another and therefore may be capable of moving independently from one another. The plurality of liquid-expandable articles may comprise a compressed material capable of a high-degree of expansion upon liquid contact.

U.S. Patent Application having Publication No. 2007/0014862 discloses, a hemostatic agent comprising oxidized cellulose in the form of a compressible, shapeable mass that can remain substantially in the compressed or shaped form for placement on a bleed site or into a wound gap. The oxidized cellulose may be a pellet of unwoven oxidized cellulose fibrous strands, or it may be strands of unwoven cellulose fibers woven or otherwise arranged into a gauze or mesh. The pellet may be compressed before being applied to the wound, which thereby allows the pellet to expand to conform to the shape of the wound gap. The pellet may be allowed to remain in the wound gap during the healing of the wound, thus causing the pellet to be absorbed by the biological processes of the body.

U.S. Patent Application having Publication No. 2006/0078589 discloses a device for treating oral wounds that form a gap and hence too large to suture. The device is intended to fill the resulting wound gap and upon contact with bleeding tissues cause local hemostasis. The device will remain in and protect the wound gap during the healing process.

U.S. Patent Publication No. 2021/0038757A1, Expandable Hemostat Composed Of Oxidized Cellulose, discloses a biodegradable hemostatic matrix comprising oxidized cellulose (OC), said OC comprising one or more sheets, wherein said matrix: (i) has a density ranging from about 0.8 to about 1.2 gr/cm$^3$, and (ii) is expandable to at least 3 times its original volume within 4 sec upon contact with an aqueous solution at at-least one temperature between 10 and 40° C.

U.S. Patent Publication No. 2008/0027365A1, Hemostatic Device With Oxidized Cellulose Pad, discloses an apparatus for promoting hemostasis, comprising: oxidized cellulose in the form of a compressible, shapeable mass that is formed into a sheet for placement on a bleed site.

U.S. Pat. No. 10,034,957, Compacted hemostatic cellulosic aggregates, discloses a method of making a plurality of hemostatic aggregates comprising the steps of: a) milling a cellulosic source material to form fibers; b) humidifying the fibers to water content of between 11.0% and 20% by weight; c) roller compacting the fibers to form hemostatic aggregates; d) sieving the hemostatic aggregates; e) dehumidifying the hemostatic aggregates to a moisture content of less than 5.5% determined by loss on drying; and f) optionally dosing the resulting hemostatic aggregates into storage containers or into delivery devices.

U.S. Pat. No. 11,007,301, Hemostatic mixture of cellulose-based short and long fibers, discloses a method of making a hemostatic composition comprising the steps of: a) reducing a size of a cellulose-based material to form long fibers and fine fibers, wherein the size distribution of the long fibers is: D90 of more than 177 μm and D50 of more than 95 μm, and wherein the size distribution of the fine fibers is: D90 of less than 177 μm, and D50 of less than 95 μm; and mixing the long and fine fibers at a ratio in the range of 5%-25% w/w and 95%-75% w/w, respectively, thereby obtaining a hemostatic fibers composition, wherein reducing the size is carried out by milling; b) optionally the hemostatic fibers composition obtained in step a) is subjected to further steps to obtain a hemostatic composition in the form of aggregates, the steps comprising: i) compacting the hemostatic fibers composition to obtain compacted hemostatic fibers composition; and optionally ii) reducing the compacted composition size.

U.S. Pat. No. 8,815,832, Oxidized regenerated cellulose hemostatic powders and methods of making, discloses a hemostatic material comprising a ball milled compacted ORC powder comprising particles having average aspect ratio from about 1 to about 18, said powder having tapped density of at least 0.45 g/cm$^3$, an average particle size of 1.75 microns to 116 microns with a median size of 36 microns and a flowability of at least 7.5 cm/s.

U.S. Pat. No. 5,823,983, Bandages comprising compressed cellulose, discloses a pressure bandage comprising: (a) a bandage comprising (i) sanitary gauze layer to be applied against a wound; (ii) a treated compressed cellulose interior layer having a grain overlying said sanitary gauze layer; and (iii) an outside layer overlying said sanitary gauze and compressed cellulose interior layers, said outside layer having adhesive wings which apply the bandage to a wound and an access hole punched therethrough and through the compressed cellulose interior layer defining a reservoir, whereby blood from the wound when absorbed through the gauze layer will saturate the compressed cellulose material and thereby expand said cellulose layer against said sanitary gauze and outer layers, thereby applying active pressure to the wound.

U.S. Patent Publication No. 2010/0184968A1, Method For Preparing An Oxidised Cellulose Compress, discloses a method for preparing an oxidized cellulose compress comprising oxidation of a cellulose based compress with a hypohalite, in the presence of an oxoammonium salt.

U.S. Patent Publication No. 2007/0014862A1, Device for treating wound gaps, discloses a hemostatic agent, comprising: oxidized cellulose in the form of a compressible, shapeable, mass that remains substantially in said compressed or shaped form for placement on a bleed site or into a wound gap.

However, since control of bleeding is essential and critical in surgical procedures to minimize blood loss, to reduce post-surgical complications, and to shorten the duration of the surgery in the operating room, there is a need of improved hemostatic forms and materials which facilitate ease of application, especially in hard-to-reach bleeding sites.

SUMMARY OF THE INVENTION

The present invention relates, in some embodiments, to compressed hemostatic tablets or forms comprising: a fibrous non-woven oxidized cellulose (OC or ORC) multilayer material compressed into a form stable tablet, further comprising calcium salt, said tablet rapidly expandable on contact with blood. The compressed forms may further comprise a multi-arm PEG-SG and are stable for at least 48 hours after compression. In some embodiments, the compressed forms upon contract with blood are expanding from 1.5 to 5 times of tablet length in 5 seconds; from 2 to 6 times of tablet length in 20 seconds; and from 3 to 6 times of tablet length in 5 minutes. The compressed forms are effective in hemostasis in heparinized blood.

In other embodiments, the compressed forms are made by compressing a stack of non-woven OC material in presence of a Calcium salt solution in ethanol, followed by drying under vacuum and evaporating said ethanol. In some embodiments, the compressed forms are made by compressing a stack of non-woven OC material in presence of a Calcium salt solution in ethanol, followed by drying under vacuum and evaporating said ethanol, followed by contacting with a solution of the multi-arm PEG-SG in a volatile solvent and vacuum drying.

In other embodiments, a method of making the compressed forms comprises the steps of: Cutting a plurality of identical pieces of the non-woven OC material; Arranging said plurality of identical pieces of the non-woven OC material in a stack; Adding a solution of the Calcium salt in ethanol into the compression die; Compressing said stack to a compression level of at least 4; Drying said stack at elevated temperature and under vacuum, allowing substantially all ethanol to evaporate, forming said stable tablet. In some embodiments, the method also comprises the steps of absorbing into the tablet of a solution of a multi-arm PEG-SG in a volatile solvent and vacuum drying said tablet; or spraying the tablet with the solution of the multi-arm PEG-SG in the volatile solvent and vacuum drying said tablet.

In some embodiments, there is provided a method of treating a wound comprising the step of applying the inventive compressed ORC forms onto and/or into the wound of a subject in a need thereof.

BRIEF DESCRIPTION OF THE DRAWINGS

FIGS. 2A, 2B and 2C present a schematic of the manufacturing method of the present compressed ORC tablets. FIGS. 2D, 2E and 2F schematically present compressed tablets of the present invention.

FIGS. 10B, 10C show the 3 mm tablet made with addition of acetone in blood.

FIG. 11A presents a plot of compressing force (g) vs. time (s) for up to 120 seconds for ORC tablets made with 10% $CaCl_2$ solution in ethanol. Also shown are the tablets after being allowed to expand.

FIG. 11E shows the initial 3 mm tablet, FIG. 11F shows this tablet after 5 sec in blood, and FIG. 11G shows this tablet after 20 sec in blood.

FIG. 11H shows the initial 5 mm tablet, FIG. 11I shows this tablet after 5 sec in blood, and FIG. 11J shows this tablet after 20 sec in blood.

FIG. 11K shows the initial 10 mm tablet, FIG. 11L shows this tablet after 5 sec in blood, and FIG. 11M shows this tablet after 20 sec in blood.

DETAILED DESCRIPTION OF INVENTIVE EMBODIMENTS

Figure 1A:
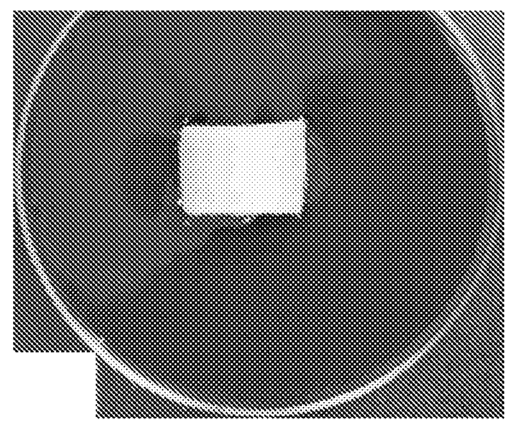
FIGS. 1A, 1B, 1C and 1D present photographs of ORC compressed forms of Table 2, taken 5 minutes after exposure and contact with blood.

The object of the present invention is to provide an expandable hemostatic tablet composition comprising oxidized cellulose (OC), more preferably oxidized regenerated cellulose (ORC) having a certain range of density, capable of high degree of expansion upon contact with body fluids, which may easily be applied to a site of need e.g., for achieving hemostasis in case of a puncture wound or a tissue gap. An advantage of the expandable composition as described herein is the ability to quickly expand into expanded form. This allows the expanded composition to quickly fill the wound cavity and provide a nearly immediate hemostatic effect without the need for applying any external pressure or compression.

Additional advantages associated with the present invention include ease of delivery in minimally invasive, laparoscopic, and/or robotic procedures, due to compact form of the inventive hemostatic tablet prior to expansion or swelling. Further advantages associated with the present invention improved positioning within the wound, improved tissue apposition and better conformation to intricate wound contours.

As explained in more detail below, the disclosed composition can be applied to a bleeding tissue and thereafter can rapidly expand upon exposing to body fluid, while taking on the shape of the wound site, enabling to assist in hemostasis. The composition can be left at the wound site as it degrades over time.

In some embodiments, the composition, being in a dry state, remains substantially in the compressed or shaped form prior to contact or placement in/on liquid media such as blood or body fluids or aqueous solutions, particularly at a bleeding site or in a wound gap.

A reference is made to U.S. Patent Publication No. 2021/0038757A1, Expandable Hemostat Composed Of Oxidized Cellulose, co-authored by one of the present inventors. For compression pressure of 2 ton pressure per 0.785 cm 2 of material, Table 2A in the cited reference lists for SNoW ORC matrix maximum expansion in saline 7.66 ml, for Fibrillar ORC matrix maximum expansion 7.66. Table 2B lists for SURGICEL, Fibrillar, SNoW ORC matrix maximum expansions 4.90, 6.86, 7.32 respectively.

Example 1. Making Comparative Samples

The compact forms expansion results of '757 Publication, as pertaining to expansion in saline, were replicated in the instant disclosure at the same parameters of testing and compression, for the same materials, with very similar maximum expansion factors, as shown below:

TABLE 1

| Replication of expansion in saline of the compressed forms made per disclosure of '757 Publication | | | | | | | |
|---|---|---|---|---|---|---|---|
| ORC materials of '757 Publication | Pressure (ton) per 0.785 $cm^2$ | Disc Weight (g) | Disc Height (cm) | Disc Diameter (cm) | Disc volume ($cm^3$) | Expansion factor at 4 sec (lengthwise) | Max Expansion factor lengthwise) |
| Fibrillar | 2 | 0.5068 | 0.524 | 1.005 | 0.4154 | 6.01 | 6.981 |
| SNoW | 2 | 0.5220 | 0.556 | 1.010 | 0.4452 | 6.51 | 6.963 |

As can be seen from Table 1, the comparative compressed forms made in this study are substantially identical and exhibiting very similar behaviors in saline as compressed forms of the '757 Publication.

The materials that referred above are SURGICEL® Original absorbable hemostat (loose knit of ORC), SURGICEL® NU-KNIT® absorbable hemostat (densely woven knit of ORC), SURGICEL® FIBRILLAR™ absorbable hemostat (soft, lightweight, layered ORC), SURGICEL® SNoW™ absorbable hemostat (structured non-woven fabric, needle punched with interlocking fibers), all available from Ethicon, Inc.

SURGICEL® Fibrillar was introduced in 1996 which provided the surgeon with a customizable non-woven form. SURGICEL® Fibrillar may be separated into layers or pulled into tufts that conform and melt into tissue quickly. The fourth member of the SURGICEL® family, SURGICEL® SNoW™ Absorbable Hemostat (SURGICEL® Structured Non-Woven) introduced in 2010. SURGICEL® SNoW™ is lightweight, drape-able and able to hold a stitch. The non-woven structure allows the product to increase surface contact with the bleeding site since it has an increased surface area, resulting in a more efficient and faster time to hemostasis which is 43% faster than SURGICEL® Original. SURGICEL® SNoW™ was designed specifically for minimally invasive surgical procedures, providing ease of use with laparoscopic tools and efficiency with product placement.

However, when the present inventors tested the replicated compact forms of '757 Publication for expansion in blood, unexpectedly the expansion was not observed. Referring to Table 2, the inventors prepared and tested in blood (5 mL, at 20 C, porcine citrated blood, placed in a petri dish 3.5 cm diameter), 10 mm diameter replicated compressed forms or tablets compressed at 2 ton per 0.785 $cm^2$, and 6 mm diameter tablets compressed at 0.72 ton per 0.785 $cm^2$, replicating '757 Publication.

TABLE 2

Figure 1B:
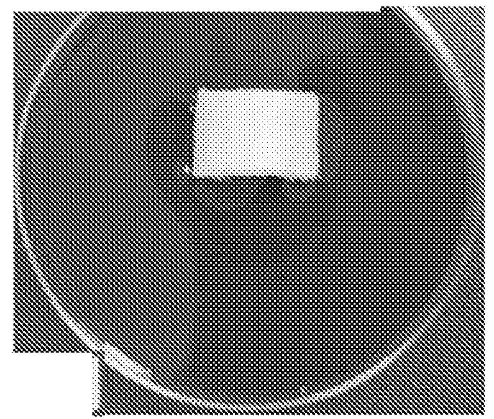
Figure 1C:
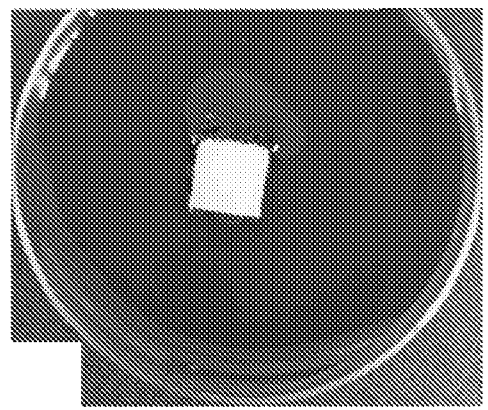
Figure 1D:
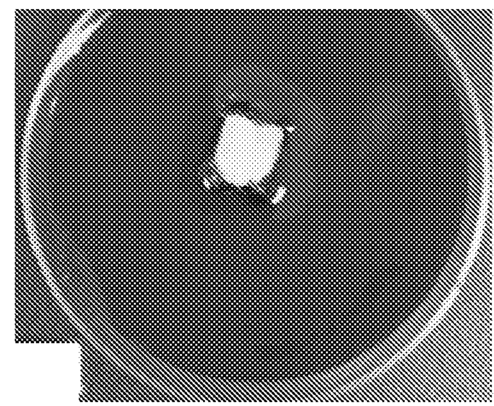

| Testing of replicated tablets made per disclosure of '757 Publication for expansion in contact with blood | | | | | | |
|---|---|---|---|---|---|---|
| ORC materials of '757 Publication for testing in blood | Pressure (ton) per 0.785 $cm^2$ | Disc Weight (g) | Disc Height (cm) | Disc Diameter (cm) | Disk volume ($cm^3$) | Expansion in blood after 5 min contact with blood |
| Fibrillar | 2 | 0.5072 | 0.526 | 1.004 | 0.4162 | None - FIG. 1a |
| SNoW | 2 | 0.5221 | 0.566 | 1.008 | 0.4514 | None - FIG. 1b |
| Fibrillar | 0.72 | 0.1830 | 0.538 | 0.6015 | 0.1528 | None - FIG. 1c |
| SNoW | 0.72 | 0.1882 | 0.564 | 0.6021 | 0.1605 | None - FIG. 1d |

FIGS. 1A-1D are presenting photographs of ORC materials of Table 2, taken 5 minutes after exposure and contact with blood, with side wall portion of the cylindrically shaped tablet facing into the blood. As seen, no expansion is observed or very minimal expansion is observed in all cases after 5 min of exposure.

Example 2. Making Compressed Orc Tablets

The present compressed ORC tablets were made of Fibrillar ORC material as follows. Referring to FIG. 2, a schematic of the manufacturing method is shown. In the first step, FIG. 2A, a 6 mm diameter punch was used to cut 10 circular pieces (total weight 0.6 g) out of Fibrillar. The cut Fibrillar was then transferred into a round die of 6 mm diameter, FIG. 2B. The 10 layers are then compressed by Texture analyzer (Model: TA.XTplusC, Serial #: 2P6Z11030-01-V003BFFC0) FIG. 2C, at a desired pressure and to desired final length (thickness), such as 10 mm, 5 mm, 3 mm The resulting compressed ORC tablet made of 10 individual disks of Fibrillar, was then pushed out of the die. For some modified compositions, various additives or binders can be added directly into the die. FIGS. 2D, 2E, 2F schematically show compressed tablets of the present invention, produced by the above methods, with all tablets being 6 mm in diameter (D), and having length (L) (or thickness or height) of 3 mm—FIG. 2D, 5 mm—FIG. 2E, and 10 mm—FIG. 2F.

Figure 3:
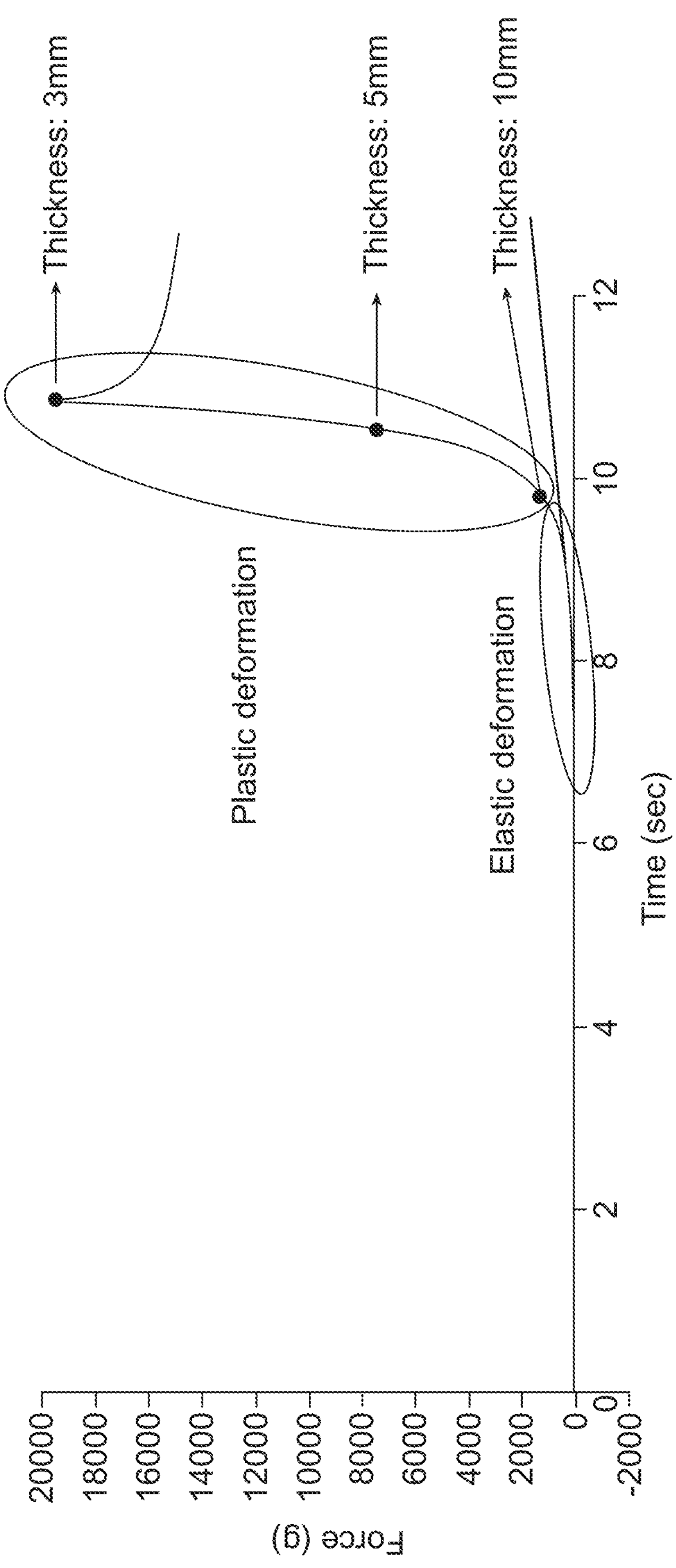
FIG. 3 presents a plot of compressing force (g) vs. time (s) for up to 11 seconds, with regions of different types of deformations identified.

For pure Fibrillar based compressed tablets, with no additives, a plot of compressing force (g) vs. time (s) for up to 11 seconds is shown in FIG. 3, with regions of different types of deformations identified, with elastic deformation resulting in the thickness of the 10 layer tablet being 10 mm, and plastic deformation at different force levels resulting in thickness of 5 mm and of 3 mm.

Example 3. Fibrillar ORC Tablets with Added Water

Figure 4:
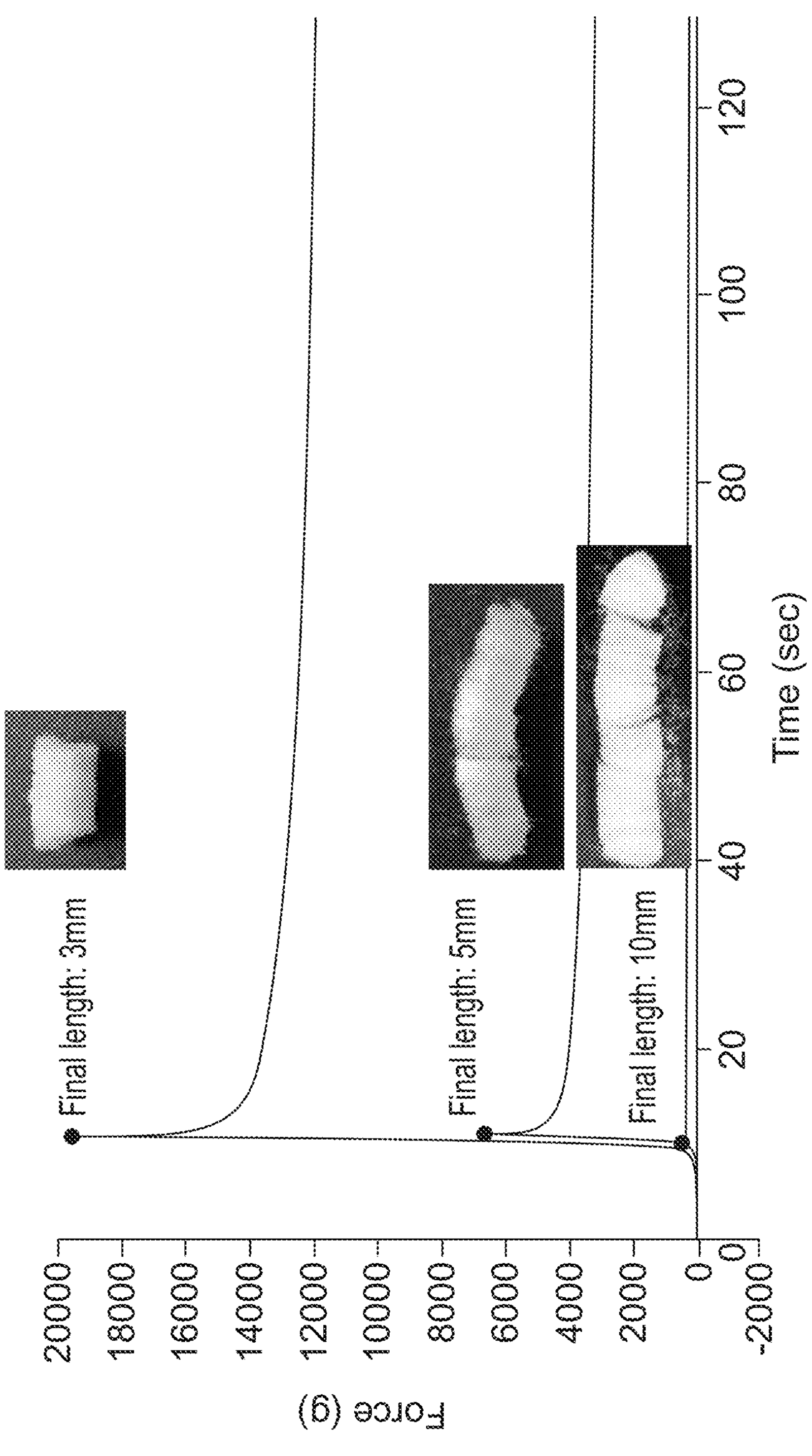
FIG. 4 presents a plot of compressing force (g) vs. time (s) for up to 120 seconds for ORC tablets compressed without added water. Also shown are the tablets after being allowed to expand.

FIG. 4 presents a plot of compressing force (g) vs. time (s) for up to 120 seconds, with the compression phase taking about 11-12 seconds, for ORC tablets compressed without added water, with longer time allowing the tablets to expand due to low stability of compressed tablets. The resulting tablets forms, all containing the same amount of ORC, are shown after being allowed to expand from their compressed length (thickness) of 10, 5, 3 mm As seen, the ORC tablets lack stability and spontaneously expand after compression, with tablet 3 mm thick or the most compressed tablet showing the least expansion after compression.

Addition of water at different levels to the Fibrillar 10-layer construct before compression has somewhat improved stability of the compressed tablets. Water was added just before compression directly into the die already containing 10 layers of Fibrillar, with water addition measured by weight of added water.

Figure 5:
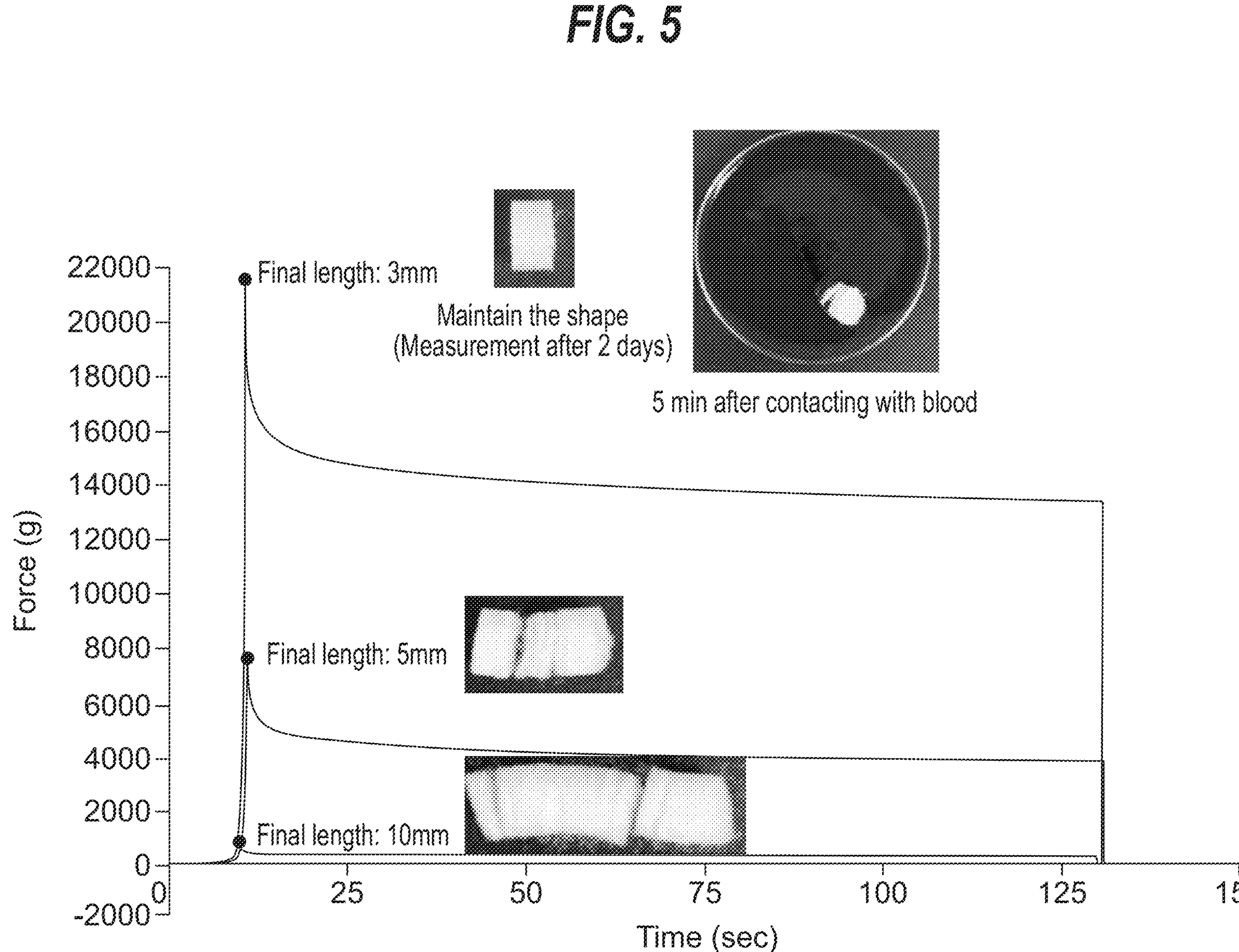
FIG. 5 presents a plot of compressing force (g) vs. time (s) for up to about 120 seconds for tablets containing added water. Also shown the tablets after being allowed to expand.

FIG. 5 presents a plot of compressing force (g) vs. time (s) for up to about 120 seconds for tablets containing 5.95% of water, with tablets that have spontaneously expanded after 2 days shown, indicating low stability of compressed tablets at 5, 10 mm length or thickness. The resulting tablet forms are shown after allowed to expand from compressed length (thickness) of 10, 5, 3 mm for 2 days. As seen, the tablet comprising 5.95% of water by weight and compressed at highest force above 21000 g to 3 mm thickness or length maintained the shape when measured 2 days after compression, while tablets compressed at lower force, such as at 7500 g, and below, failed to maintain shape. Also shown in FIG. 5 is the 3 mm tablet comprising 5.95% water immersed into blood, showing none to very limited expansion even at 5 min after blood contact.

Figure 6:
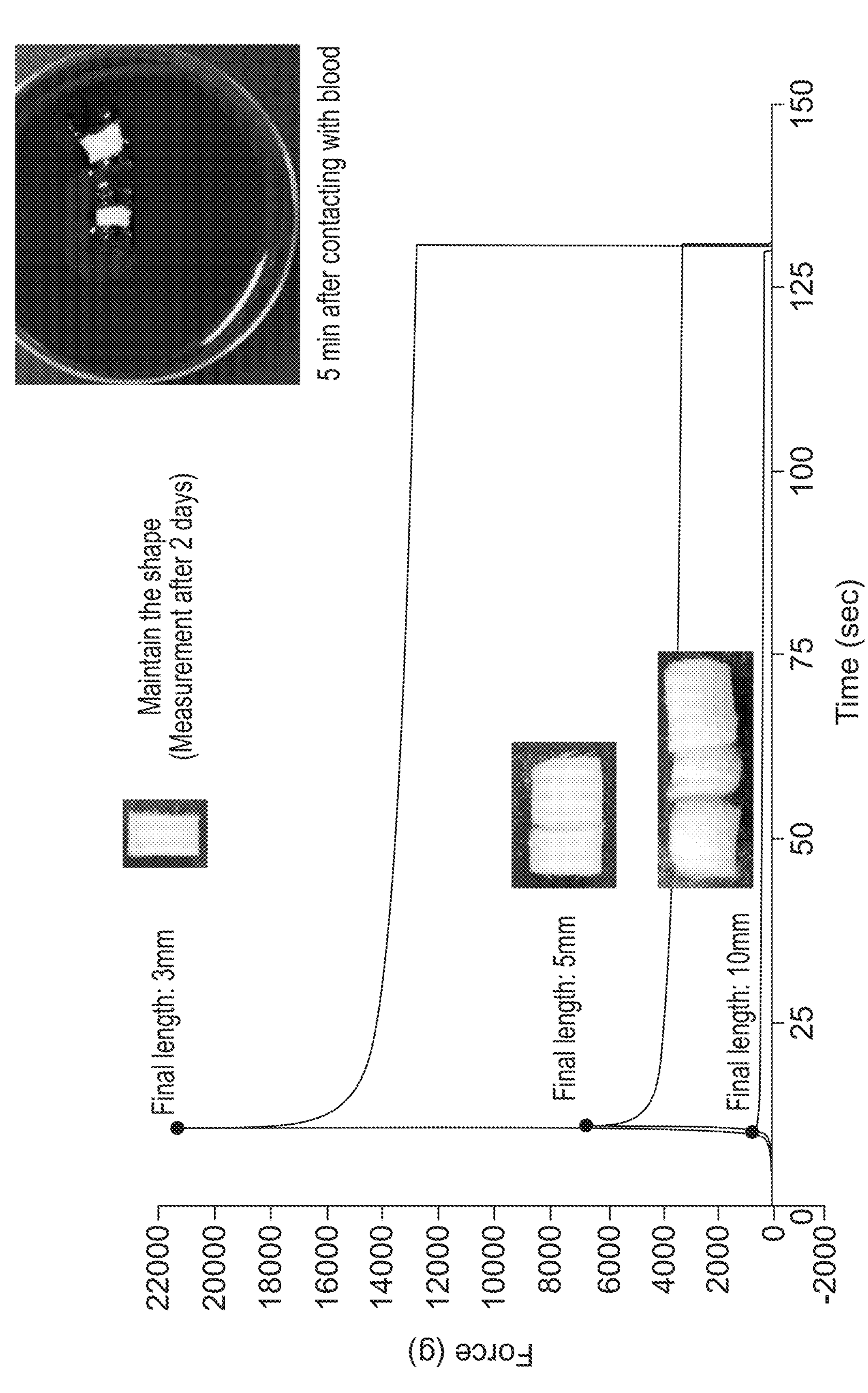
FIG. 6 presents a plot of compressing force (g) vs. time (s) for up to about 120 seconds for tablets containing added water. Also shown the tablets after being allowed to expand.

Similarly, FIG. 6 presents a plot of compressing force (g) vs. time (s) for up to about 120 seconds for tablets containing 8.68% of water, with expanded tablets shown indicating low stability of compressed tablets at 5, 10 mm length after 2 days. The resulting tablets forms are shown after allowed to expand from compressed length (thickness) of 10, 5, 3 mm As seen, the tablet comprising 8.68% of water by weight and compressed at highest force above 21000 g to 3 mm thickness or length maintained the shape when measured 2 days after compression, while tablets compressed at lower force, such as at 7500 g, and below, failed to maintain shape. Also shown in FIG. 6 is the 3 mm tablet comprising 8.68% water immersed into blood, showing none to very limited expansion even at 5 min after blood contact.

Figure 7:
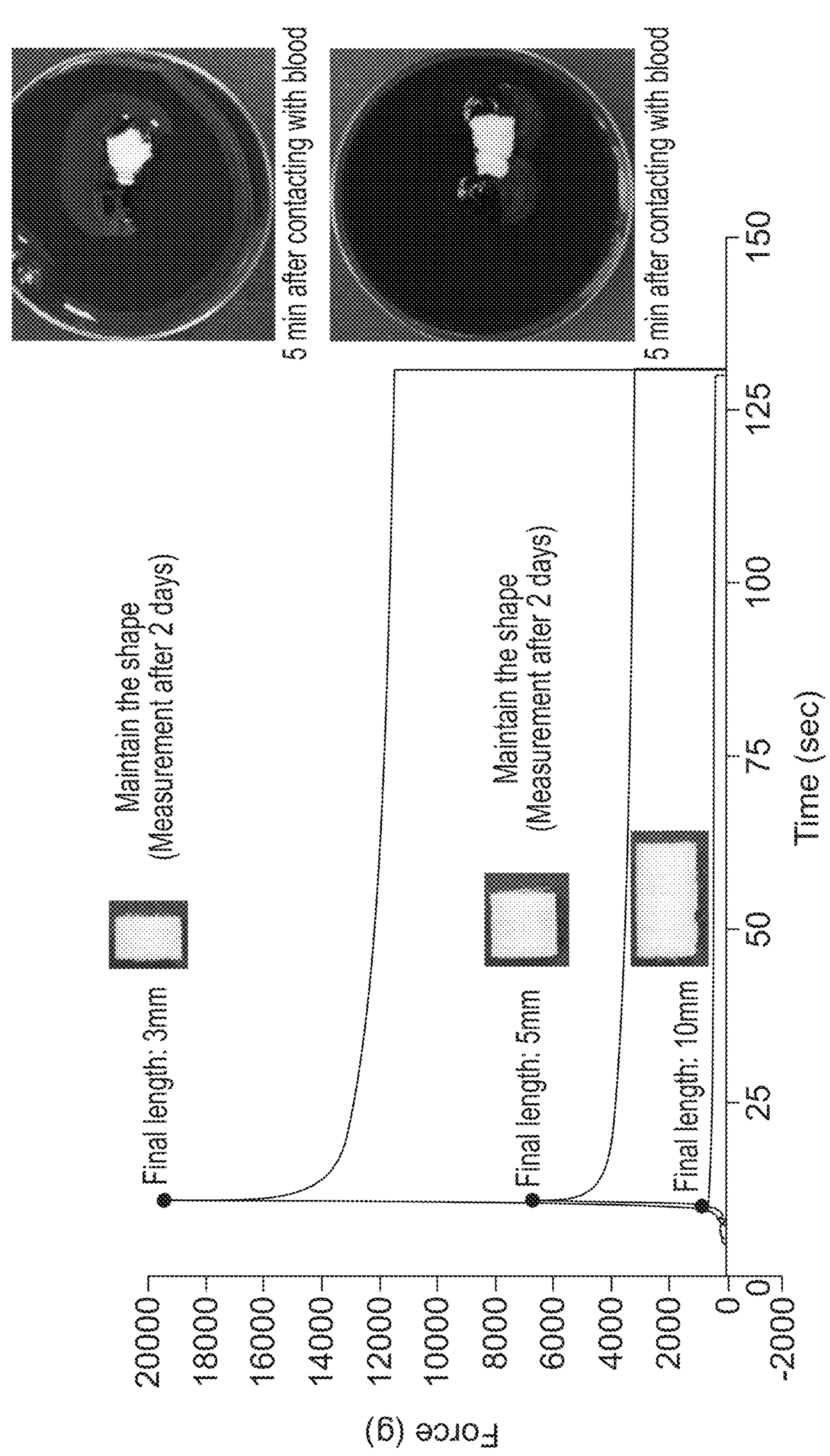
FIG. 7 presents a plot of compressing force (g) vs. time (s) for up to about 120 seconds for tablets containing added water Also shown the tablets after being allowed to expand.

Similarly, FIG. 7 presents a plot of compressing force (g) vs. time (s) for up to about 120 seconds for tablets containing 13.23% of water, with expanded tablets shown indicating low stability of compressed tablets at 10 mm length. The resulting tablets forms are shown after allowed to expand from compressed length (thickness) of 10, 5, 3 mm As seen, the tablet comprising 13.23% of water by weight and compressed at highest force above 21000 g to 3 mm thickness or length and the tablet compressed at force of about 7000 g to 5 mm thickness or length have maintained the shape when measured 2 days after compression. Tablets compressed at lower force, failed to maintain shape. Also shown in FIG. 6 is the 3 mm tablet comprising 13.23% water immersed into blood, and 5 mm tablet comprising 13.23% water immersed into blood, both tablets showing none to very limited expansion even 5 min after blood contact.

The results of testing are summarized in Table 3.

TABLE 3

Testing of compressed Fibrillar ORC tablet containing water

| | Dry tablet (0% water) | 5.95% water content | 8.68% water content | 13.23% water content |
|---|---|---|---|---|
| Maintaining tablet shape - measured after 2 days | 10 mm - failed<br>5 mm - failed<br>3 mm - failed | 10 mm - failed<br>5 mm - failed<br>3 mm - good | 10 mm - failed<br>5 mm - failed<br>3 mm - good | 10 mm - failed<br>5 mm - good<br>3 mm - good |
| Expansion in blood | Not tested | 10 mm -not tested<br>5 mm - not tested<br>3 mm -very slow expansion, less than 20% even after 5 min | 10 mm -not tested<br>5 mm - not tested<br>3 mm- very slow expansion, less than 20% even after 5 min | 10 mm -not tested<br>5 mm, 3 mm- very slow expansion, less than 20% even after 5 min |

The above data shows that presence of moisture and compressing to 3 mm thick results in stability, and for 5 mm tablets also stability at 13% of water, with other samples not stable. None of the tablets show fast and significant expansion upon exposure to blood.

Example 4. Fibrillar Orc Tablets with Added Solvents

Figures 8A, 8B, 8C, 8D, 8E, 8F:
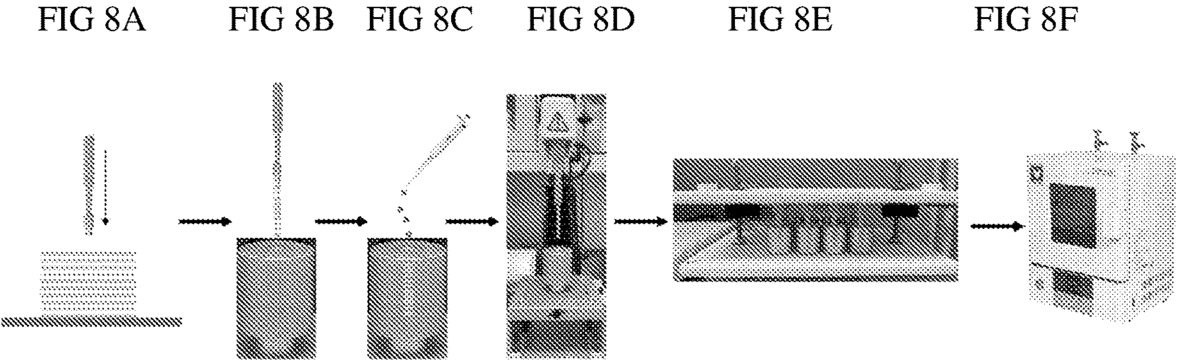
FIGS. 8A, 8B, 8C, 8D, 8E and 8F present a schematic of the manufacturing method of the present compressed ORC tablets.

Similar to the process described above, and referring to FIG. 8, a schematic of the manufacturing method is shown. In the first step, a 6 mm punch was used to cut 10 circular pieces (total weight 0.6 g) out of Fibrillar (FIG. 8A). The cut Fibrillar was then transferred into a round die of 6 mm diameter (FIG. 8B). 1 ml of pure solvent (ethanol or acetone) was then added into the die and absorbed by the Fibrillar material (FIG. 8C). The 10 layers were then compressed by Texture analyzer (FIG. 8D) as described above at a desired pressure and to desired final length (thickness), such as 10 mm, 5 mm, 3 mm A bi-layer plate was then used to clamp several dies with compressed tablets inside (FIG. 8E), the tablets being held inside the die by the compression piston. The whole die was then put into a vacuum oven (Yamato Scientific Co., Model: ADP300C, Serial #: J3080178) equipped with a cold trap (Yamato Scientific Co., Model: CA301, Serial #: 63700976) at 70 C, −0.08 MPa for drying for 3 hours (FIG. 8F), allowing solvents to evaporate. The resulting compressed ORC tablet made of 10 individual disks of Fibrillar, was then pushed out of the die.

Figure 9A:
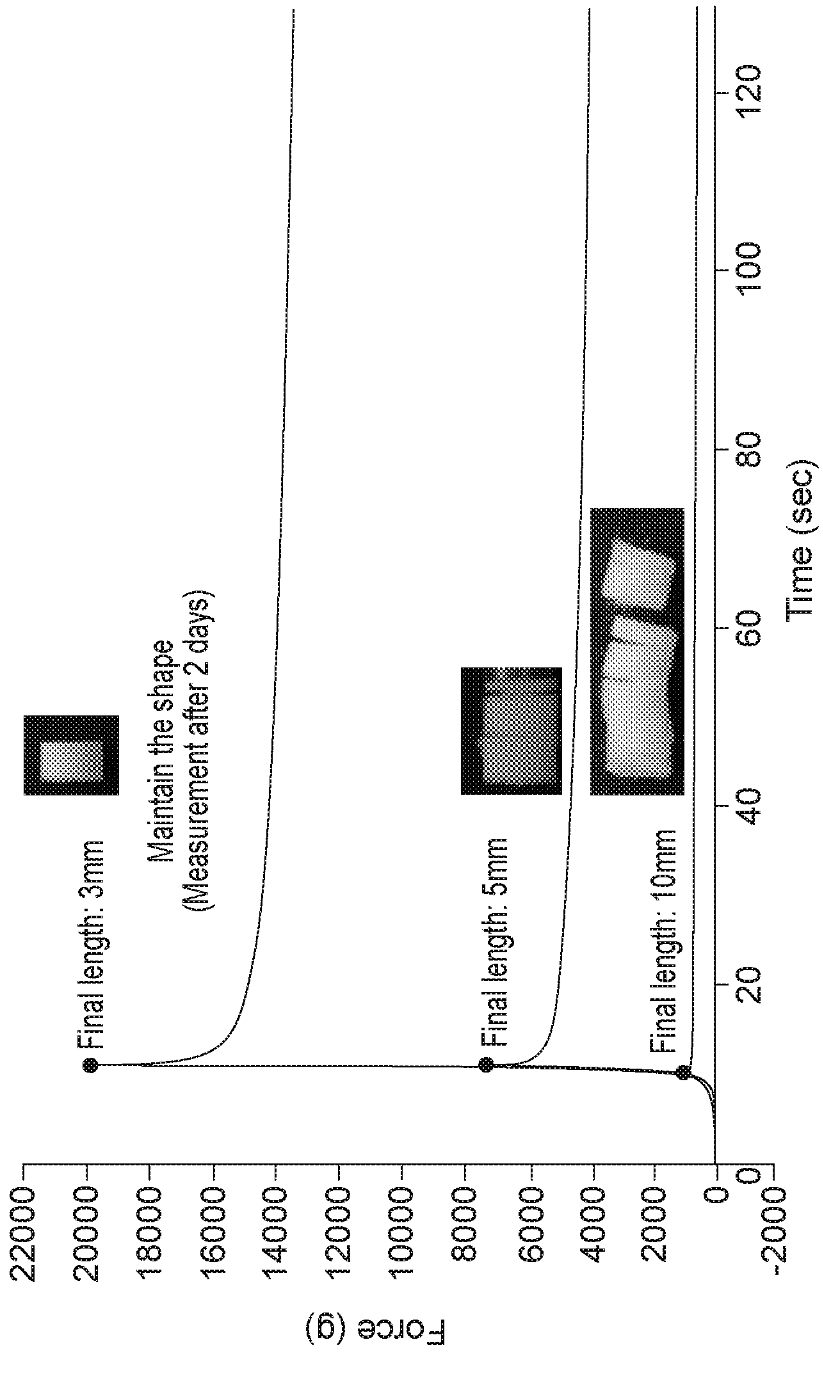
FIG. 9A presents a plot of compressing force (g) vs. time (s) for up to 120 seconds for ORC tablets made with Ethanol. Also shown are the tablets after being allowed to expand.

Similar to characterization of ORC tablets with added water described above, tablets made with solvents were tested as follows. FIG. 9A presents a plot of Fibrillar ORC tablets made with Ethanol, showing compressing force (g)

vs. time (s) for up to 120 seconds. Tablets made with Ethanol at lower compression forces, as shown, indicate low stability of compressed tablets at 5, 10 mm length or thickness. The resulting tablets forms are shown after allowed to expand from compressed length (thickness) of 10, 5, 3 mm As seen, the tablet compressed at highest force at about 20000 g to 3 mm thickness or length maintained the shape when measured 2 days after compression, while 5 and 10 mm tablets compressed at lower force, such as at 7500 g, and below, failed to maintain shape and spontaneously expanded.

Figure 9B:
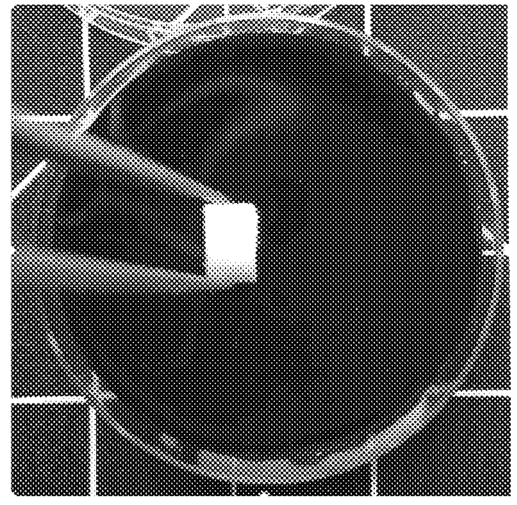
FIGS. 9B, 9C show the 3 mm tablet made with addition of Ethanol in blood.
Figure 9C:
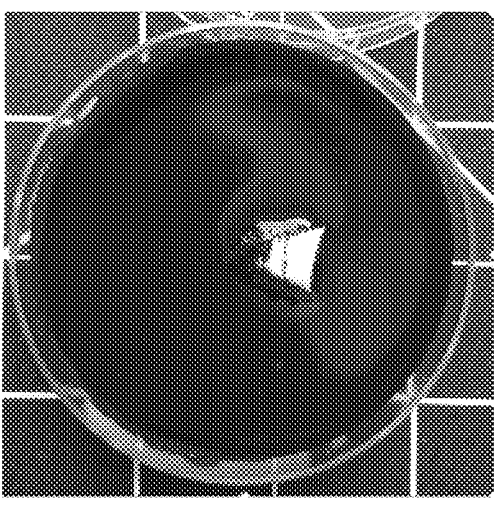

FIGS. 9B, 9C show the 3 mm tablet made with addition of Ethanol in blood, at the beginning of immersion, and at 30 seconds, with no substantial expansion.

Figure 10A:
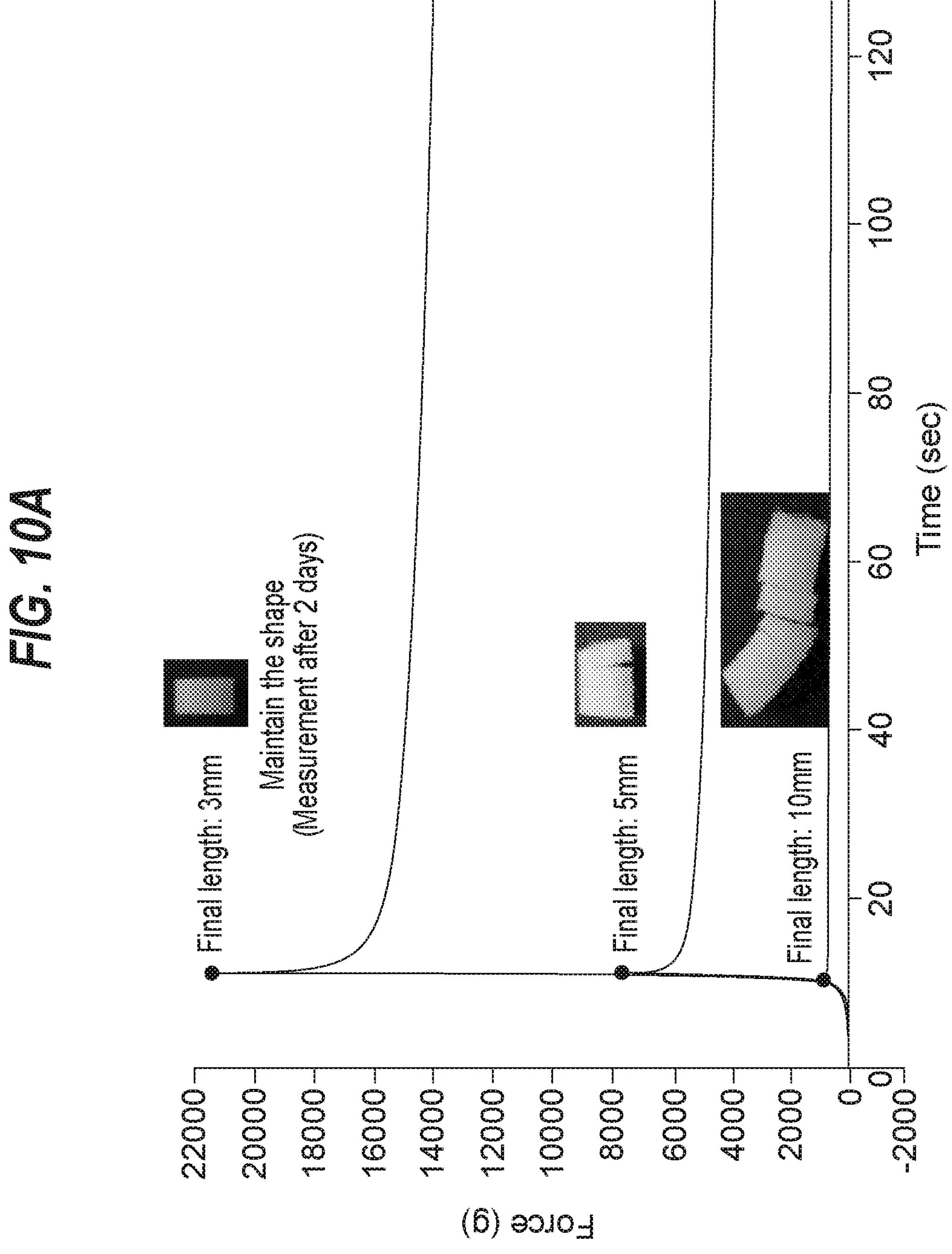
FIG. 10A presents a plot of compressing force (g) vs. time (s) for up to 120 seconds for ORC tablets made with acetone. Also shown are the tablets after being allowed to expand.

FIG. 10A presents a plot of Fibrillar ORC tablets made with acetone, showing compressing force (g) vs. time (s) for up to 120 seconds. Tablets made with acetone at lower compression forces, as shown, indicate low stability of compressed tablets at 5, 10 mm length or thickness. The resulting tablets forms are shown after allowed to expand from compressed length (thickness) of 10, 5, 3 mm As seen, the tablet compressed at highest force at about 21500 g to 3 mm thickness or length maintained the shape when measured 2 days after compression, while tablets compressed at lower force, such as at 7500 g, and below, failed to maintain shape and spontaneously expanded.

Figures 10B, 10C:
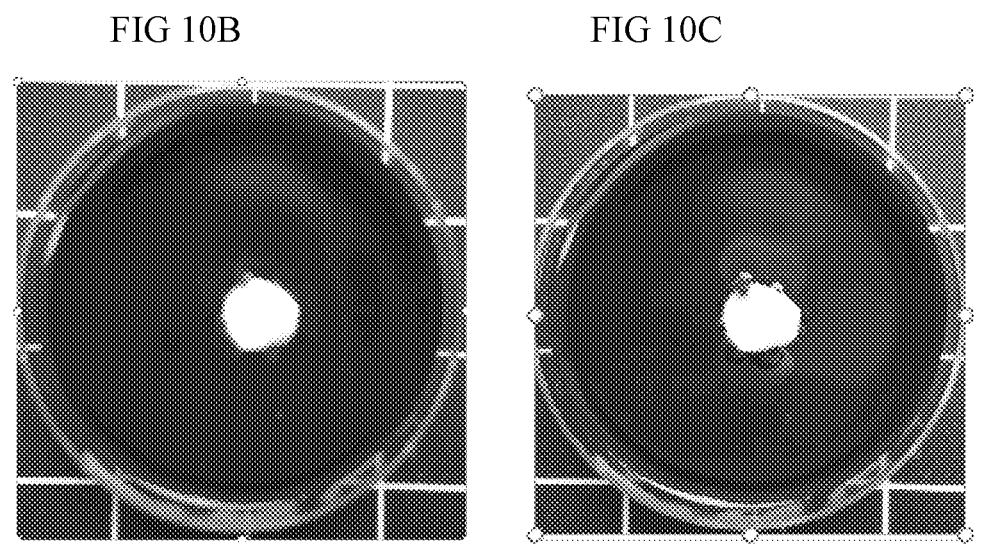

FIGS. 10B, 10C show the 3 mm tablet made with addition of acetone in blood, at the beginning of immersion, and at 30 seconds, with no substantial expansion.

Even stable compressed ORC tablet forms made with solvents show virtually no expansion in blood.

Example 5. Fibrillar Orc Tablets Made with $CaCl_2$ and Ethanol

Similar to the process described above, inventive compressed ORC tablets were made with addition of various concentrations of $CaCl_2$ in Ethanol to Fibrillar before compression. After the Fibrillar was transferred into a round die of 6 mm diameter, 1 ml of ethanol containing a variable amount of $CaCl_2$ was added directly into the die and absorbed by the Fibrillar material. The 10 layers were then compressed by Texture analyzer as described above at a desired pressure and to desired final length (thickness), such as 10 mm, 5 mm, 3 mm A bi-layer plate was then used to clamp several dies with compressed tablets inside, the tablets being held inside the die by the compression piston. The whole die was then put into a vacuum oven at 70 C, −0.08 MPa for drying for 3 hours, allowing ethanol to evaporate. The resulting compressed ORC tablet made of 10 individual disks of Fibrillar, and containing certain amount of added $CaCl_2$ was then pushed out of the die and tested.

FIG. 11A presents a plot of ORC tablets made with 10% $CaCl_2$ solution in ethanol, showing compressing force (g) vs. time (s) for up to 120 seconds. Tablets made with Ethanol and 10% $CaCl_2$ show good stability at all compression forces and at all lengths or thicknesses after 2 days, as shown, indicating good stability of compressed tablets at 3, 5, 10 mm length or thickness.

Figures 11B, 11C, 11D:
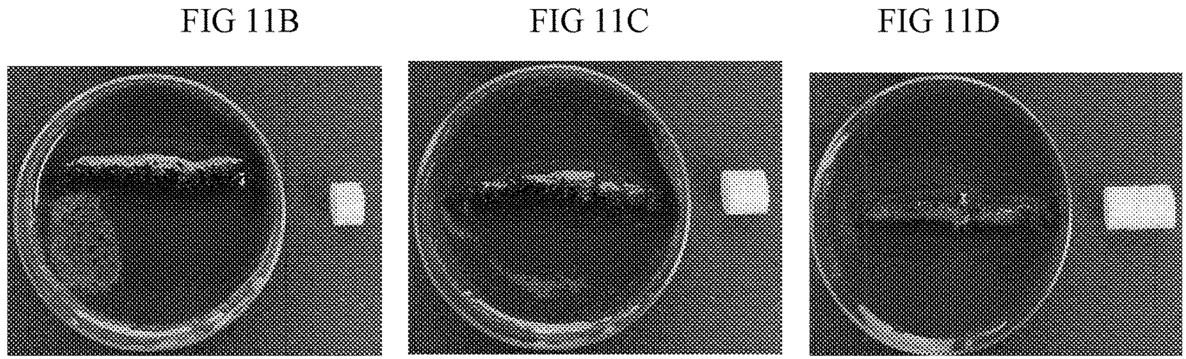
FIGS. 11B, 11C and 11D show the initial tablets and tablets after allowed to react with blood and to expand in blood after 5 minutes of blood contact.

FIGS. 11B-D show the initial tablets and tablets after allowed to react with blood and to expand in blood after 5 minutes of blood contact. FIG. 11B shows 3 mm tablet, FIG. 11C shows 5 mm tablet, and FIG. 11D shows 10 mm tablet.

FIG. 11E shows the initial 3 mm tablet, FIG. 11F shows this tablet after 5 sec in blood, and FIG. 11G shows this tablet after 20 sec in blood.

FIG. 11H shows the initial 5 mm tablet, FIG. 11I shows this tablet after 5 sec in blood, and FIG. 11J shows this tablet after 20 sec in blood.

FIG. 11K shows the initial 10 mm tablet, FIG. 11L shows this tablet after 5 sec in blood, and FIG. 11M shows this tablet after 20 sec in blood.

The data indicates very rapid expansion of all compressed ORC tablets were made with addition of various concentrations of $CaCl_2$ in Ethanol, with expansion within 5s, 20s, 5 min shown in the Table 3A.

TABLE 3A

Expansion of compressed ORC tablets made with Ethanol and 10% $CaCl_2$ in blood

| | Expanded within 5 sec | Expanded within 20 sec | Expanded after 5 min |
|---|---|---|---|
| 3 mm tablet | 5 times the tablet length or more | 6 times the tablet length or more | 6 times the tablet length or more |
| 5 mm tablet | 3 times the tablet length or more | 4 times the tablet length or more | 5 times the tablet length or more |
| 10 mm tablet | 1.5 times the tablet length or more | 2 times the tablet length or more | 3 times the tablet length or more |

The results show that all tablets, including 3, 5, 10 mm length and compressed at low, medium, and high compression force, demonstrate very substantial and rapid expansion upon contact with blood. All compressed tablets reach expanded length of at least one half of the initial length of the ORC stack prior to compression, such as 50%, 60%, 75%, 80% of the initial ORC stack prior to compression.

Figure 12:
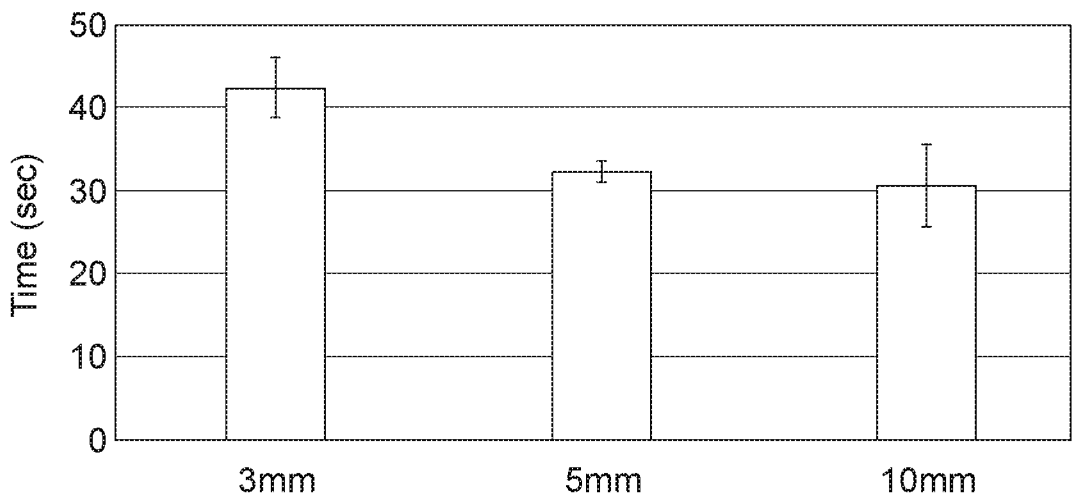
FIG. 12 shows time that was required for the compressed Fibrillar ORC tablet containing 10% $CaCl_2$ and made with ethanol (F-10Ca-Et) to expand to 3.5 cm in length.

FIG. 12 shows time that was required for the compressed Fibrillar ORC tablet containing 10% $CaCl_2$ and made with ethanol (F-10Ca-Et) to expand to 3.5 cm in length, with 3 mm tablet taking about 42 s, 5 mm tablet 32 s, 10 mm-31 s.

Figure 13:
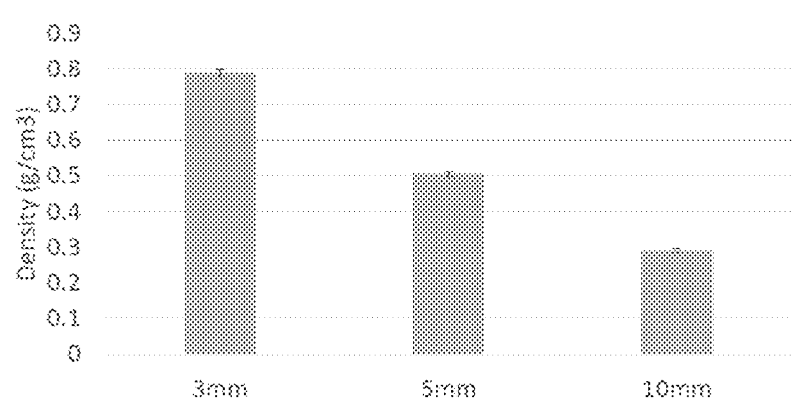
FIG. 13 shows density of F-10Ca-Et tablet.

FIG. 13 shows density of F-10Ca-Et tablet.

Figure 14:
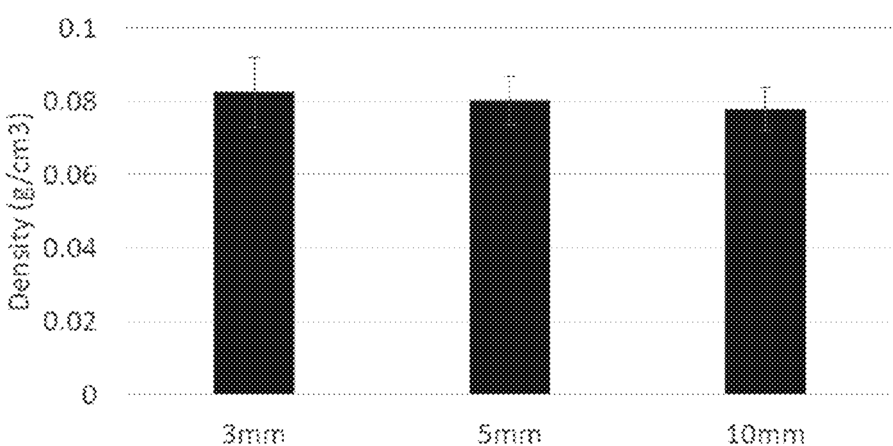
FIG. 14 shows $CaCl_2$ content in the tablets in g/cm 3 of F-10Ca-Et tablet.

FIG. 14 shows $CaCl_2$ content in the tablets in g/cm 3 of F-10Ca-Et tablet.

Table 4 shows comparative data of testing compressed ORC tablets that were made with solvents and with addition of $CaCl_2$. As seen, the F-10Ca-Et compressed ORC tablets show excellent performance at all compression levels and thicknesses, for both stability and expansion in blood.

TABLE 4

Testing of compressed Fibrillar ORC tablets with solvents and $CaCl_2$

| | Tablet made with Ethanol | Tablet made with Acetone | F-10Ca-Et Fibrillar ORC tablet containing 10% $CaCl_2$ and made with ethanol |
|---|---|---|---|
| Maintaining tablet shape - measured after 2 days | 10 mm - failed<br>5 mm - failed<br>3 mm - no change | 10 mm - failed<br>5 mm - failed<br>3 mm - no change | 10 mm - no change<br>5 mm - no change<br>3 mm - no change |
| Expansion in blood | 3 mm- very slow, less | 3 mm- very slow, less | 10 mm - significant expansion, at |

TABLE 4-continued

Testing of compressed Fibrillar ORC tablets with solvents and $CaCl_2$

| Tablet made with Ethanol | Tablet made with Acetone | F-10Ca-Et Fibrillar ORC tablet containing 10% $CaCl_2$ and made with ethanol |
|---|---|---|
| than 20% expansion in 5 min | than 20% expansion in 5 min | least 100%, with blood penetrating into the entire tablet<br>5 mm - significant expansion, at least 100%, with blood penetrating into the entire tablet<br>3 mm - significant expansion, at least 100%, with blood penetrating into the entire tablet |

Figure 15A:
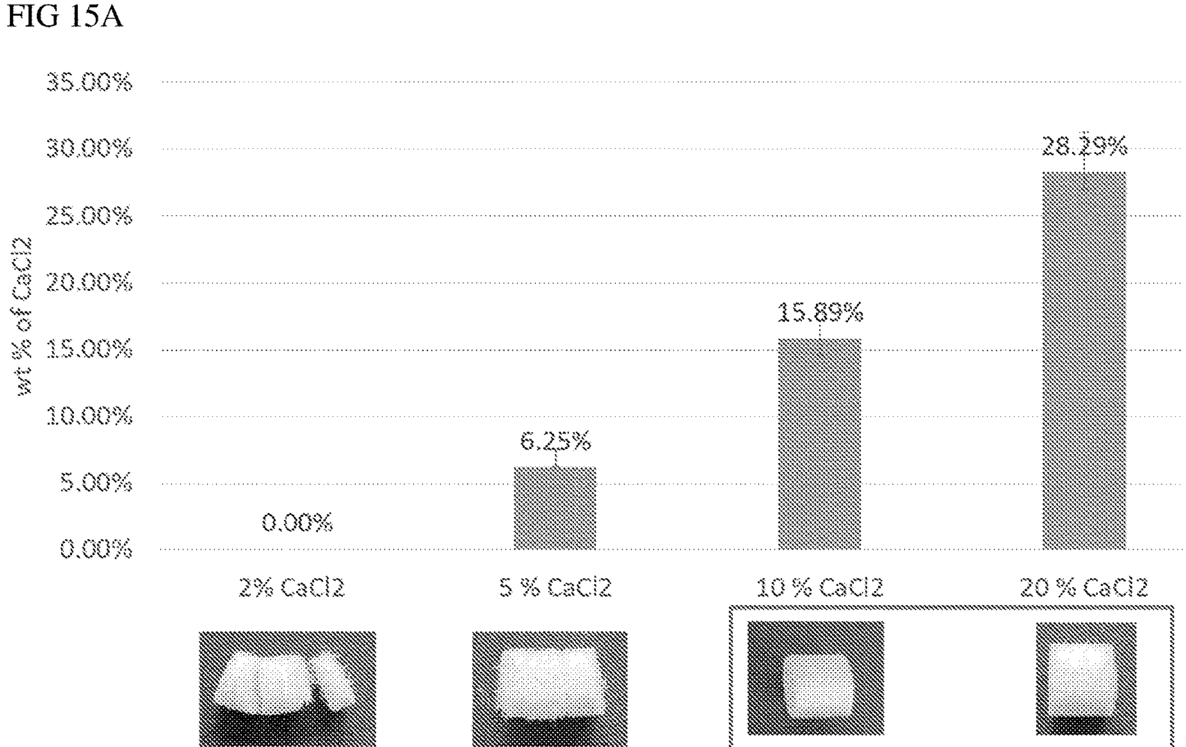
FIG. 15A shows the results of testing of 5 mm length compressed ORC tablets containing variable amounts of added $CaCl_2$.

Further testing was performed for variable concentrations of $CaCl_2$ in 5 mm Fibrillar tablets made with $CaCl_2$ ethanol solutions as follows. FIG. 15A shows the results of testing of 5 mm length compressed ORC tablets containing variable amounts of added $CaCl_2$, with weight % of $CaCl_2$ in the final tablet shown vs. concentration of $CaCl_2$ in ethanol. As seen, adding 10% and 20% $CaCl_2$ in ethanol resulted in tablets maintaining the shape after 2 days, while lower $CaCl_2$ concentrations have failed to maintain shape and spontaneously expanded within 2 days.

Figures 15B, 15C, 15D, 15E, 15F, 15G:
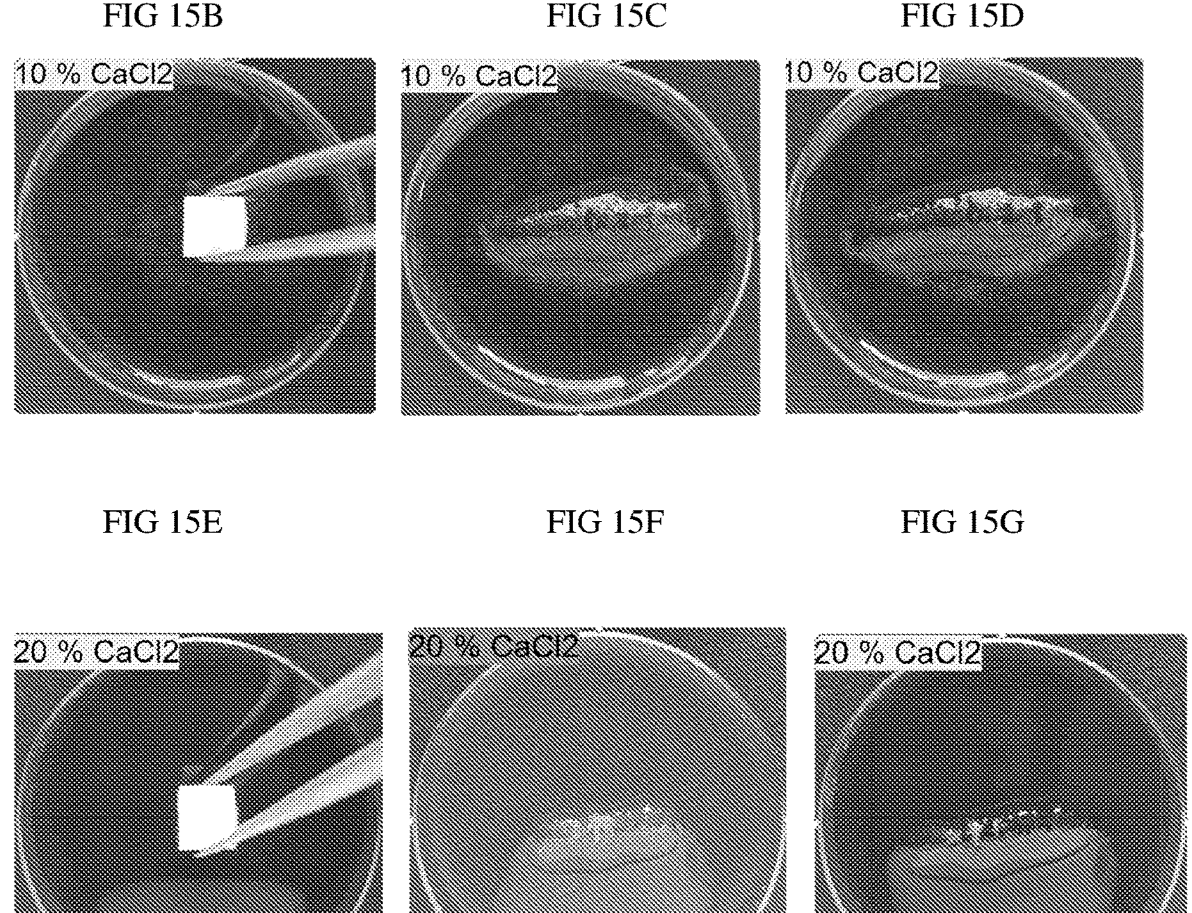
FIG. 15B shows the initial 5 mm tablet F-10Ca-Et.
FIG. 15C shows this tablet after 5 sec in blood.
FIG. 15D shows this tablet after 20 sec in blood.
FIG. 15E shows the initial 5 mm F-20Ca-Et.
FIG. 15F shows this tablet after 5 sec in blood.
FIG. 15G shows this tablet after 20 sec in blood.

Referring to FIGS. 15B-D, FIG. 15B shows the initial 5 mm Fibrillar tablet made with 10% $CaCl_2$ ethanol solution (F-10Ca-Et), FIG. 15C shows this tablet after 5 sec in blood, and FIG. 15D shows this tablet after 20 sec in blood.

Referring to FIGS. 15E-G, FIG. 15E shows the initial 5 mm Fibrillar tablet made with 20% $CaCl_2$ ethanol solution (F-20Ca-Et), FIG. 15F shows this tablet after 5 sec in blood, and FIG. 15G shows this tablet after 20 sec in blood.

The data presented indicates that tablets made with 10% $CaCl_2$ solutions compositions (F-10Ca-Et) not only maintained the shape, but also expanded in blood very fast. Tablets made with 20% $CaCl_2$ solutions compositions (F-20Ca-Et) maintained the shape, but expanded in blood slower than F-10Ca-Et. Fibrillar compositions at 2% and 5% of added $CaCl_2$ ethanol solutions, F-2Ca-Et and F-5Ca-Et, have failed to maintain the shape and were not tested in blood.

Figure 16:
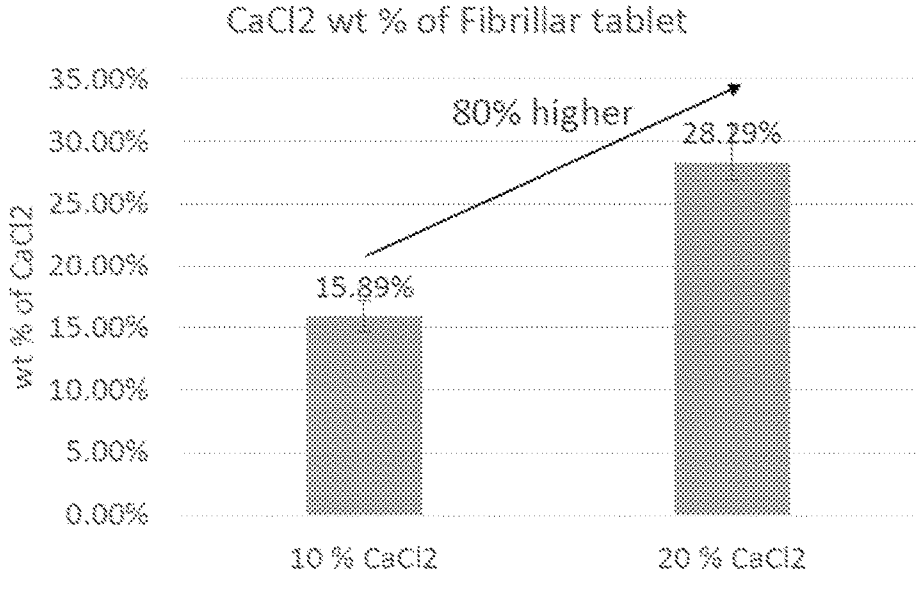
FIG. 16 presents for 5 mm compressed tablets, weight % concentration of $CaCl_2$.
Figure 17:
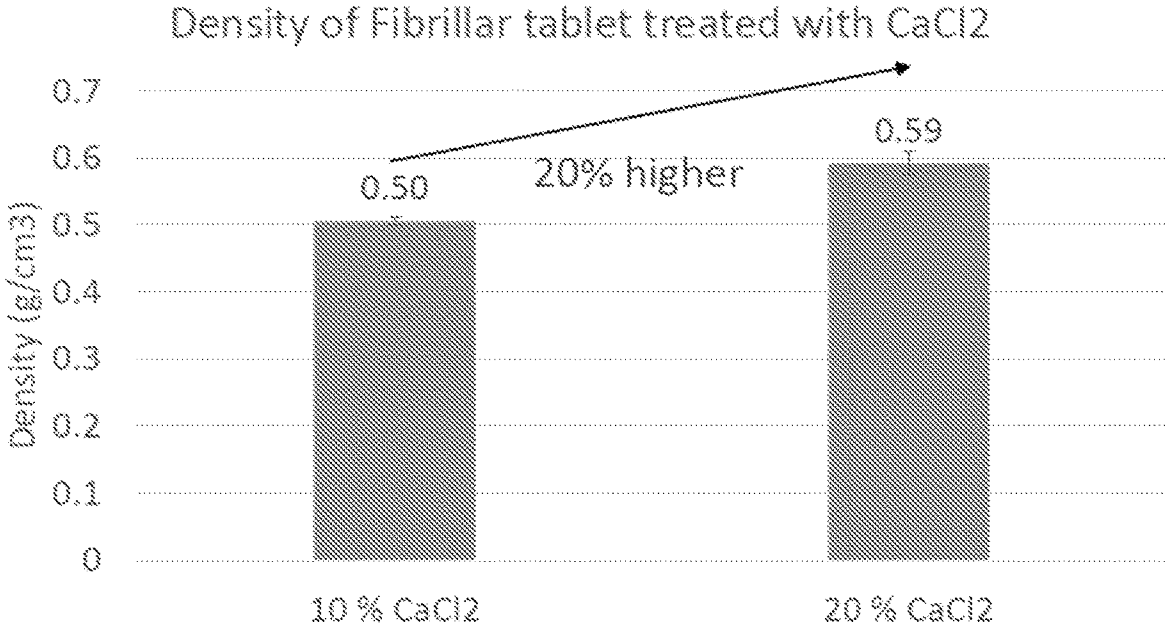
FIG. 17 presents density of F-10Ca-Et and F-20Ca-Et tablets.

FIG. 16 presents for 5 mm compressed tablets, weight % concentration of $CaCl_2$ in final Fibrillar ORC forms for F-10Ca-Et and F-20Ca-Et, estimated at 15.89% for F-10Ca-Et and 28.29% for F-20Ca-Et. FIG. 17 presents density of F-10Ca-Et and F-20Ca-Et, estimated at 0.50 and 0.59 respectively.

Further testing in animal model was performed for F-10Ca-Et and F-20Ca-Et Fibrillar ORC tablets.

The animal used in this study was a female juvenile porcine with a weight of 55-70 kg. The bleeding model was set as the 6 mm biopsy punch (3 mm deep) on the liver or spleen. Female porcine was put on a fast for 24 hours prior to the surgical procedure. The animal was anesthetized with 1150-1400 mg Ketamine, 115-140 mg Xylazine, 7.5 mg Midazolam. Anesthesia was maintained with Isoflurane and the abdomen was opened to reveal the spleen. Mean arterial blood pressure, body temperature and heart rate were continuously monitored throughout the surgical procedure. The experiment was terminated when mean arterial blood pressure dropped below 60 mmHg An 8 mm diameter×3 mm depth biopsy punch was carried out on the spleen and the specimen was excised with surgical scissors. The punch site was allowed to bleed for 30 seconds and bleeding intensity was visually assessed on a scale of 0-5 (as described in FIG. 7); "no bleeding" was given a score of 0 and "intensive bleeding" was given a score of 5. Next, the punch site was wiped with clean gauze to remove excess blood and a single tablet was inserted into the puncture wound. Thereafter, the bleeding rate was re-evaluated. 2-minute manual compression was applied and followed by a 30-second observation time. If the hemostasis was not achieved during the 30-second observation time, another 30-second manual compression was applied, followed by another 30-second observation time. Time-to-hemostasis was determined when hemostasis was successfully achieved within the 5 minutes and to be categorized as successful (pass). At 5 minutes, if bleeding was still persisting, the trial was aborted as a failure and recorded as ">5 minutes" (greater than 5 minutes).

For a heparinized model, a mature, about 60 kg, female porcine was treated as described above, with abdomen being opened to reveal the liver or spleen, and with 27,000 IU of Heparin being administered prior to biopsy procedure. ACT (Activated Clotting Time) test was used in order to monitor the Heparin treatment. Accordingly, Heparin boosts were given in order to maintain stable ACT levels. Heparin is used as an injectable anticoagulant (through antithrombin III activation) and therefore this model represents a challenging bleeding model.

The liver was subjected to 8 mm diameter×3 mm depth biopsy punch. The Porcine spleen was subjected to 6 mm diameter×3 mm depth biopsy punch. In both organs, the specimen was excised with surgical scissors. The punch site was allowed to bleed for 30 seconds and bleeding intensity (level) was visually assessed on a scale of 0-5, as described above. The hemostatic efficacy evaluation was performed in the porcine liver and in the porcine spleen. The ORC tablets were manually applied to the wound sites.

The results of testing are presented in Table 5.

TABLE 5

Testing of F-10Ca-Et and F-20Ca-Et ORC tablets in animal models

| Sample | Non-heparinized liver punch (porcine) | Heparinized liver punch (porcine) | Heparinized spleen punch (porcine) |
|---|---|---|---|
| F-20Ca-Et | passed | passed | failed |
| F-10Ca-Et | passed | passed | passed |

As shown, F-10Ca-Et tablet was working in all models, including Non-heparinized liver punch (porcine), Heparinized liver punch (porcine), Heparinized spleen punch (porcine), while F-20Ca-Et worked in Non-heparinized liver punch (porcine), Heparinized liver punch (porcine), but failed in Heparinized spleen punch (porcine).

Example 6. Snow Orc Tablets with $CaCl_2$ and Ethanol

Similar to the process described above, compressed ORC forms were made of SNoW ORC materials, by cutting 18 circular pieces out of SNoW. The cut circular pieces of SNoW were then transferred into a round die of 6 mm diameter for addition of ethanol, $CaCl_2$, and compression, followed by drying as described above. The 18 layers of ORC are compressed by Texture analyzer at a desired pressure and to desired final length (thickness), such as 10 mm, 5 mm, 3 mm Referring to FIG. 18, a comparative is shown with 18 layers of SNoW prior to compression (A) being about the same thickness as 10 layers of Fibrillar (B), corresponding to the thickness or length 4-4.5 cm pre-compression. Post-compression both materials are yielding 5 mm long tablets as shown SNoW-C and Fibrillar-D, expanding to very similar expanded forms at 3-3.5 cm long, SNoW-E and Fibrillar-F, with at least 5 times expansion, more preferably 6 times expansion or more, most preferably over 7 times expansion.

Figures 18A, 18B, 18C, 18D, 18E, 18F:
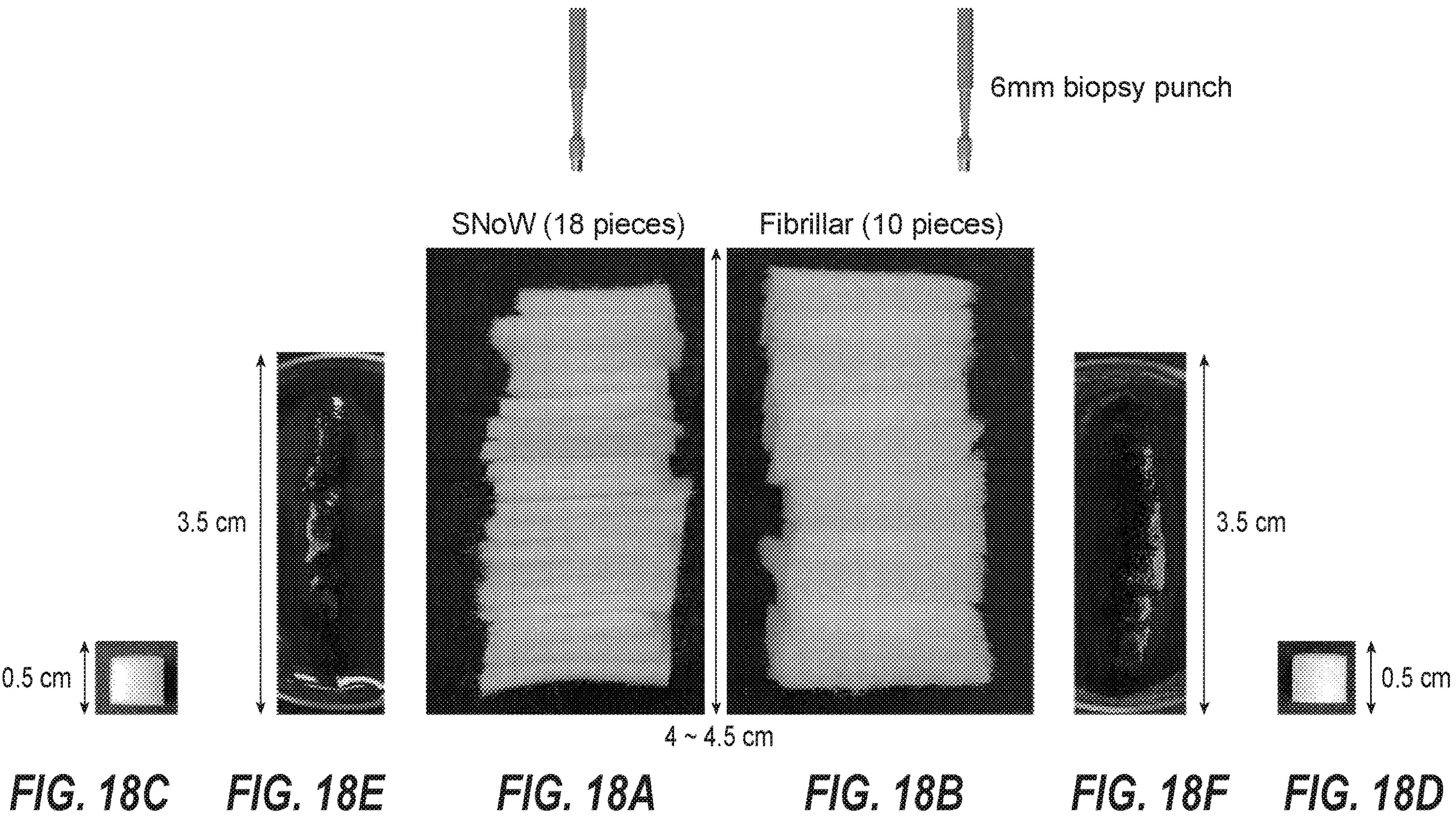
FIGS. 18A-B presents a comparative schematics of layers of SNoW prior to compression (A) vs layers of Fibrillar (B).
FIGS. 18C-D show post-compression tablets as shown SNoW-C and Fibrillar-D.
FIGS. 18E-F show expanded tablets in blood, SNoW-E and Fibrillar-F.

As shown in FIG. 18, non-woven ORC materials are compressed from an initial stack of 4-4.5 cm length or height to tablets that are 3, 5, 10, mm long (thick), i.e. the compression ratio, defined as original length of the stack (free standing, unweighted, uncompressed discs resulting from 6 mm diameter punch) divided by the final tablet length, is about 13-15 for 3 mm tablets, 8-9 for 5 mm tablets, and 4-4.5 for 10 mm tablets. Overall, compression ratio is 4-15 for all tablets or 8-15 for 5, 3 mm tablets. The maximum expansion of 5 mm tablets is to over 3-3.5 cm, or over 6-7 times.

Figure 19:
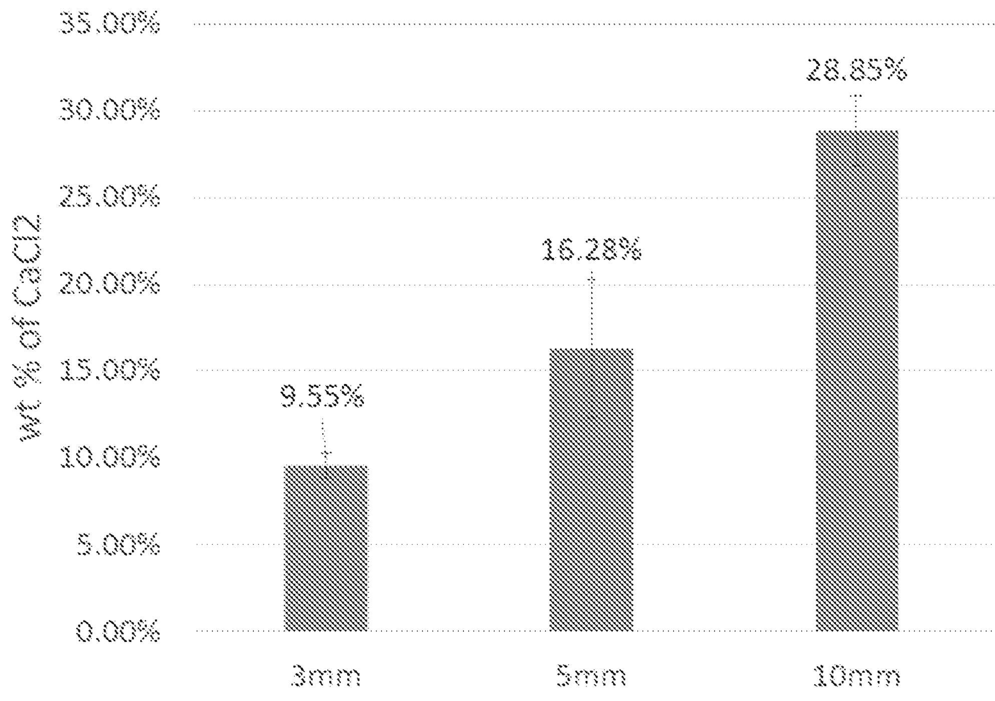
FIG. 19 shows $CaCl_2$ weight % of the final SNoW compressed ORC tablets S-10Ca-Et at 3, 5, 10 mm thickness.

FIG. 19 shows $CaCl_2$ weight % of the final SNoW compressed ORC tablet made with 10% $CaCl_2$ in ethanol (S-10Ca-Et) at 3, 5, 10 mm thickness corresponding to 9.55%, 16.28%, 28.85% respectively.

Figure 20:
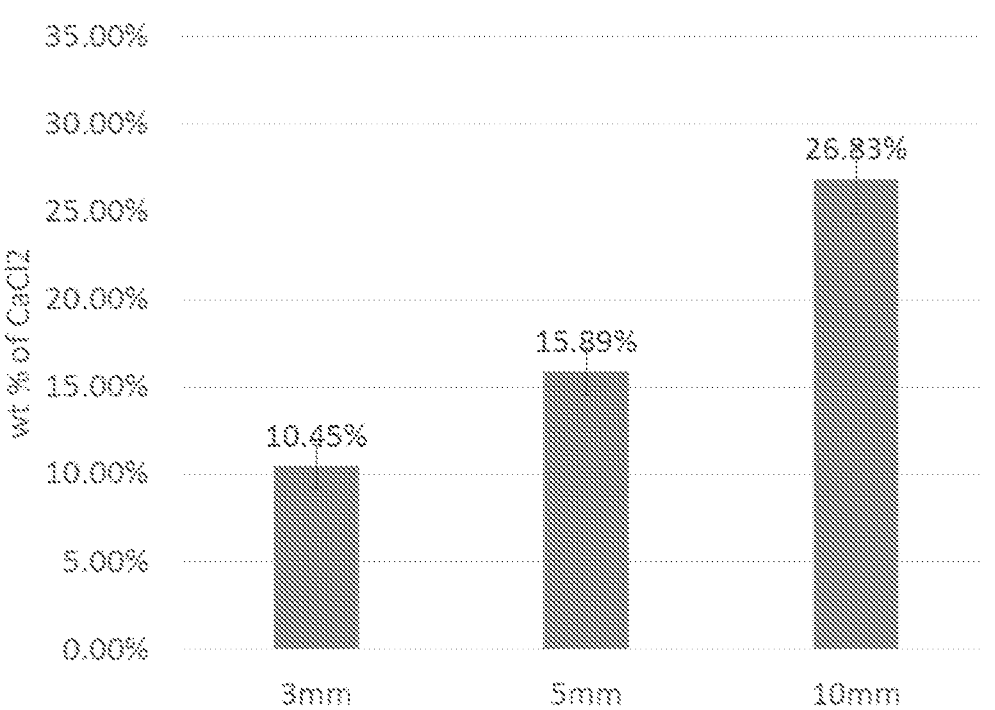
FIG. 20 shows $CaCl_2$ weight % of the final Fibrillar compressed ORC tablet F-10Ca-Et at 3, 5, 10 mm thickness.

FIG. 20 shows $CaCl_2$ weight % of the final Fibrillar compressed ORC tablet made with 10% $CaCl_2$ in ethanol (F-10Ca-Et) at 3, 5, 10 mm thickness corresponding to similar concentrations, 10.45%, 15.89%, 26.83% respectively.

Example 7. Compressed Fibrillar Orc Tablets with $CaCl_2$ and Ethanol Further Comprising 4-Arm Peg-Sg-10K The inventors have further discovered that it is advantageous to incorporate multi-arm polyethylene glycol functionalized with PEG-SG, Succinimidyl Glutarate (or PEG-NHS). An acetone solution of 10 kDa 4 arm PEG-SG, designated as PEG-SG-10K was prepared at 0.2 g/ml.

In the first, absorption, method of making the compressed tablet, the already prepared 5 mm long F-10Ca-Et ORC tablets as described above were treated by slowly adding 90 microliters of 0.2 g/ml PEG-SG-10K acetone solution onto the ORC tablet from a micropipette, until the solution was fully absorbed into the tablet. The tablet was then placed into vacuum at 4 torr for 12 hours to fully evaporate the solvent. The resulting tablets, made by the absorption method, F-10Ca-Et-SGa contained 0.018 g of PEG-SG-10K per tablet.

In the second, spraying, method of making the compressed tablet, the already prepared 5 mm long F-10Ca-Et ORC tablets as described above were treated by spraying 0.2 g/mL PEG-SG-10K acetone solution onto the ORC tablet from a spray bottle. The tablet was then placed into vacuum at 4 ton for 12 hours to fully evaporate the solvent. The resulting tablets, made by the spraying, F-10Ca-Et-SGs contained the same amount of 0.018 g of PEG-SG-10K per tablet.

Figure 21A:
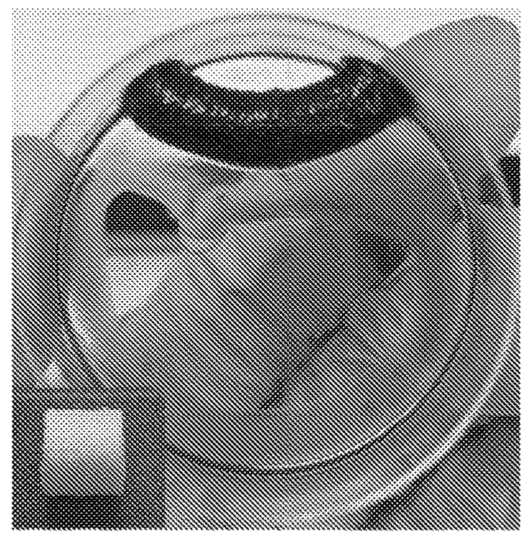
FIGS. 21A and 21B show results of testing of tablets F-10Ca-Et-SGa made by absorbent method.
Figure 21B:
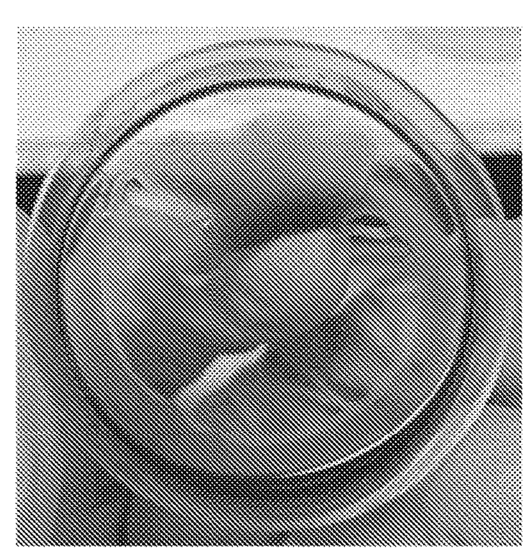

Referring now to FIG. 21A, testing of tablets F-10Ca-Et-SGa made by absorbent method, demonstrates good expansion when exposed to 1 ml of porcine citrated blood, after 2 minutes contact in a Petri dish. However, while good expansion is observed, there is some non-clotted blood around the expanded tablet as shown, particularly visible in FIG. 21B, after removal of tablet F-10Ca-Et-SGa.

Figure 22A:
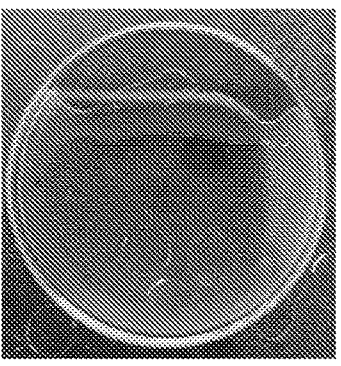
FIGS. 22A, 22B, 22C, show the results of testing of tablets F-10Ca-Et-SGs made by spraying method.
Figure 22B:
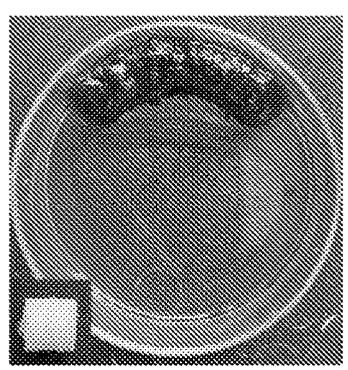
Figure 22C:
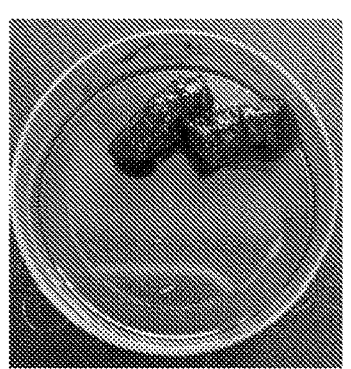

Referring now to FIG. 22A,22B, 22C, testing of tablets F-10Ca-Et-SGs made by spraying method, shows good expansion when exposed to 1 ml of porcine citrated blood, after 2 minutes contact. While good expansion is observed, advantageously there is less non-clotted blood around the expanded tablet.

Ex-Vivo and In-Vivo Testing of Compressed Orc Tablets

Further testing was performed in various models to evaluate performance of the embodiments of the present invention. Table 6 shows various samples tested in the following Examples.

TABLE 6

Samples tested Ex-Vivo and In-Vivo

| Sample | Description | Format | Shape | Size (Diameter × Thickness) | Weight of ORC per tablet, g | Weight of $CaCl_2$ per tablet (Average), g | Weight of PEGSG10K per tablet (Average), g |
|---|---|---|---|---|---|---|---|
| 1 | F-10Ca-Et Fibrillar treated with 10% $CaCl_2$ in EtOH | Tablet | Cylinder | 6 mm × 5 mm | 0.06 | 0.011 | N/A |
| 2 | F-20Ca-Et Fibrillar treated with 20% $CaC1_2$ in EtOH | Tablet | Cylinder | 6 mm × 5 mm | 0.06 | 0.024 | N/A |
| 3 | F-10Ca-Et-SGs Fibrillar treated with 10% $CaCl_2$ in EtOH & sprayed with 0.2 g/ml of 4 arm-PEGSG10K in Acetone | Tablet | Cylinder | 6 mm × 5 mm | 0.06 | 0.011 | 0.02 |
| 4 | F-10Ca-Et-SGa Fibrillar treated with 10% $CaCl_2$ in EtOH & enriched with 0.2 g/ml of 4 arm-PEGSG10K in Acetone | Tablet | Cylinder | 6 mm × 5 mm | 0.06 | 0.011 | 0.02 |

TABLE 6-continued

| Samples tested Ex-Vivo and In-Vivo | | | | | | | |
|---|---|---|---|---|---|---|---|
| Sample | Description | Format | Shape | Size (Diameter × Thickness) | Weight of ORC per tablet, g | Weight of $CaCl_2$ per tablet (Average), g | Weight of PEGSG10K per tablet (Average), g |
| 5 | S-10Ca-Et-SGs SNoW treated with 10% $CaCl_2$ in EtOH & sprayed with 0.2 g/ml of 4 arm-PEGSG10K in Acetone | Tablet | Cylinder | 6 mm × 5 mm | 0.06 | 0.012 | 0.02 |
| 6 | Control - Fibrillar | Patch | Square patch | 13 mm (Length) | 0.06 | N/A | N/A |

Example 8. Ex-Vivo Burst Test: Heparinized Kidney Biopsy Punch Model

The testing was performed in Biopsy Punch model, with Heparinized bovine whole blood. Anticoagulation ratio: 1:99 (1000 IU/ml Na heparin to whole blood). Studied organ: Porcine kidney, purchased from Farm to Pharm LLC. Biopsy Punch (ID): 4 mm Mean Arterial Pressure at Defect Creation: 20 mmHg. Tamponade period: 2 min. Observation period: 30 sec. Definition of "Pass" and "Fail": Pass: Hemostasis was maintained during observation period; Fail: Could not achieve hemostasis during observation period Experimental procedure: The test article was applied over the bleeding defect; 2-minute manual compression was applied and followed by a 30-second observation time. If the hemostasis was not achieved during the 30-second observation time, the trial was aborted as "Fail". If the hemostasis was achieved, it is considered as "Pass" and followed by increasing the blood pressure to test the maximum burst value.

The results of the ex-vivo burst tests are presented in Table 7.

TABLE 7

| Ex-vivo burst test results | | | | | |
|---|---|---|---|---|---|
| Sample # | # of Trial | Biopsy punch (ID) | Mean Arterial Pressure at Defect Creation | Hemostasis maintained during observation period (Pass/Fail) | Max blood pressure at burst point |
| 1 | 1 | 4 mm | 20 mmHg | P | 135 mmHg |
| 1 | 2 | 4 mm | 20 mmHg | P | 60 mmHg |
| 2 | 1 | 4 mm | 20 mmHg | F | N/A |
| 2 | 2 | 4 mm | 20 mmHg | P | 100 mmHg |
| 3 | 1 | 4 mm | 20 mmHg | P | 82 mmHg |
| 3 | 2 | 4 mm | 20 mmHg | P | 138 mmHg |
| 4 | 1 | 4 mm | 20 mmHg | P | 109 mmHg |
| 6 (control) | 1 | 4 mm | 20 mmHg | F | N/A |

The analysis of test results indicates that control sample No. 6 has failed. Sample No. 2 has failed in one test and passed in one. All other samples have passed all tests.

Example 9. In-Vivo Animal Study: Heparinized Porcine Hepatic Biopsy Punch Model

The testing was performed in as follows. Animal species: Porcine; Gender: Female; Age: Juvenile; Weight: 55-70 kg; Studied organ: Liver; Biopsy Punch (ID×Thickness): 6 mm×3 mm; Initial tamponade period: 2 min; Observation period: 30 sec; Time to hemostasis: the time period from the test article was applied to achieve hemostasis; Definition of "Pass" and "Fail": Pass: Achieved hemostasis within 5 minutes; Fail: Could not achieve hemostasis within 5 minutes.

Experimental Procedure: The test article was applied over the bleeding defect. 2-minute manual compression was applied and followed by a 30-second observation time. If the hemostasis was not achieved during the 30-second observation time, another 30-second manual compression was applied, followed by another 30-second observation time. Time-to-hemostasis was determined when hemostasis was successfully achieved within the 5 minutes and to be categorized as successful (pass). At 5 minutes, if bleeding was still persisting, the trial was aborted as a failure and recorded as ">5 minutes" (greater than 5 minutes).

A Female Yorkshire swine (Animal No. 56251, Animal Biotech Industries, Inc.) weighing 68 kg was used for the hemostasis testing, respectively. The animals were ear-tagged and acclimated at the testing facility for at least 3 days before any procedure was conducted. This animal was individually housed, fed once a day with standard pig chow, and had access to water ad libitum. Housing and husbandry conformed to the standards of the "Guide for the Care and Use of Laboratory Animals". The study was conducted by CRF Skirball Center for Innovation, Orangeburg, NY, USA in their AAALAC International accredited facility. Animal protocols were reviewed and approved by CRF Skirball Center for Innovation's Institutional Animal Care and Use Committee (IACUC). An in-vivo porcine liver biopsy punch model was utilized to compare the hemostatic performance of the test materials. This animal was anesthetized with intramuscular injections of a combination of TZed (210 mg/2.1 mL) and Glyco (0.28 mg/1.4 mL) followed by endotracheal intubation and maintenance of anesthesia by inhalation of 2% isoflurane mixed with 100% oxygen (1 L/min). Mechanical ventilation (10-20 mL/kg, 10-15 respirations/minute) was used throughout the procedure. The marginal ear vein of each pig was catheterized for delivery of fluids and drugs as needed. Lactated Ringer's solution or saline was administered intravenously (IV) throughout the surgical procedure. Blood pressure was measured intraarterially in the carotid artery using a catheter connected to a transducer. Heart and respiratory rates (HR, RR), electrocardiography (ECG), CO2, body temperature, and mean arterial blood pressure (MAP) were monitored continuously. Fluid infusion rate was adjusted as needed to maintain physiologic blood pressure levels.

The exposed liver was kept moist using saline-soaked gauzes. The animal was first heparinized with an activated clotting time of 344-417 seconds. The bleeding defect was created by using a 6 mm biopsy punch 3 mm deep on the liver. The test article was first applied to the bleeding defect. 2-minute manual compression was applied and followed by a 30-second observation time. If the hemostasis was not achieved during the 30-second observation time, another 30-second manual compression was applied, followed by another 30-second observation time. Time-to-hemostasis was determined when hemostasis was successfully achieved within the 5 minutes and to be categorized as successful (pass). At 5 minutes, if the bleeding was still persisting, the trial was aborted as a failure and recorded as ">5 minutes" (greater than 5 minutes).

The results of the in-vivo tests are presented in Table 8.

TABLE 8

In-vivo test results

| Sample # | Trial # | Activated Clotting Time(ACT) Baseline Value/Value | Biopsy punch (Diameter × thickness) | Bleeding Level | Mean Arterial Pressure at Defect Creation | Hemostasis Achieved within 5 min (Pass/Fail) | Time to Hemostasis |
|---|---|---|---|---|---|---|---|
| 1 | 1 | 124 sec/ 372 sec | 6 mm × 3 mm | Severe | 82 mmHg | P | 4 min |
| 2 | 1 | 124 sec/ 344 sec | 6 mm × 3 mm | Severe | 81 mmHg | F | >5 min |
| 3 | 1 | 124 sec/ 417 sec | 6 mm × 3 mm | Severe | 88 mmHg | P | 2 min |
| 4 | 1 | 124 sec/ 372 sec | 6 mm × 3 mm | Severe | 90 mmHg | P | 2 min |
| 5 | 1 | 124 sec/ 372 sec | 6 mm × 3 mm | Severe | 83 mmHg | P | 2 min |
| 6 (control) | 1 | 124 sec/ 372 sec | 6 mm × 3 mm | Mild | 79 mmHg | F | >5 min |

The analysis of test results indicates that control sample No. 6 has failed. Sample No. 2 has failed. Sample No. 1 has passed and achieved hemostasis, but only at a longer time of 4 minutes. Samples 3-5 containing PEG-SG all have passed and achieved hemostasis at a short time of 2 min.

The preferred embodiments are:

Compressed non-woven ORC, such as Fibrillar, treated with 10% $CaCl_2$ in EtOH or F-10Ca-Et The most preferred embodiments are:

Compressed non-woven ORC, such as Fibrillar, treated with 10% $CaCl_2$ in EtOH & sprayed with 0.2 g/ml of 4 arm-PEGSG10K in Acetone or F-10Ca-Et-SGs;

Compressed non-woven ORC, such as Fibrillar, treated with 10% $CaCl_2$ in EtOH & enriched with 0.2 g/ml of 4 arm-PEGSG10K in Acetone or F-10Ca-Et-SGa; and Compressed non-woven ORC, such as SNoW, treated with 10% $CaCl_2$ in EtOH & sprayed with 0.2 g/ml of 4 arm-PEGSG10K in Acetone or S-10Ca-Et-SGs.

The preferred embodiments are multi-layer compressed OC forms, more preferably ORC forms, more preferably made of non-woven ORC materials.

The preferred embodiments of compressed ORC tablets are stable after compression and do not spontaneously expand when not exposed to bodily fluids, blood, but rapidly expand and swell when in contact with blood and or bodily fluids.

The preferred embodiments are made by combining multi-layer ORC construct with $CaCl_2$ in ethanol prior to compression.

The preferred embodiments are made by combining multi-layer ORC construct with $CaCl_2$ in ethanol prior to compression.

The preferred embodiments are made by combining multi-layer ORC construct with $CaCl_2$ in ethanol prior to compression and further comprise PEG-SG.

The preferred embodiments comprise compressed multi-layer ORC tablets comprising $CaCl_2$ and multi-arm PEG-SG.

In some embodiments, the tablet may be applied manually, or, in some embodiments, using a device such as a medical device, e.g., trocar (of various dimensions e.g., a diameter of 5, 10, 12, 15 mm, etc.,), or other known applicators. Depending on shape, form and size desired for the contemplated use, different molds or other compression techniques may be used to achieve the desired body of the disclosed tablets or compositions.

The compressed ORC tablets may be in any shape or form, e.g., having a substantially, polygonal or rectangular (including substantially square), substantially circular and/or substantially oval cross-section along at least one axis. For example, the tablets may have a substantially box-like shape, having a substantially rectangular cross-section (optionally with rounded corners) along 3 axes; a substantially cylindrical shape, having substantially circular and/or substantially oval cross-section along one axis, and a substantially rectangular cross-section (optionally with rounded corners) along 2 axes; or a substantially spherical or ovoid shape, having a substantially circular and/or substantially oval cross-section along 3 axes. Other shapes, forms and sizes of the disclosed composition may be selected from, without being limited thereto, plugs, disks, rods, tubes, conical cylinders, spheres, half and spheres, cubes, rectangles, triangles, or saucers.

In some embodiments, the volume of the tablet may be greater than 1 $mm^3$. In some embodiments, the volume of the tablet may be at least 5 $mm^3$. In some embodiments, the volume of the matrix may be greater than 10 $mm^3$. In some embodiments, the volume of the tablet may be about 5, 10, 15, 20, 25, 30, 35, 40, 45, 50, 55, 60, 65, 70, 75, 80, 85, 90, 95, or 100 $mm^3$, including any value and range therebetween. In some embodiments, the volume of the tablet may be greater than 100 $mm^3$. In some embodiments, the volume of the tablet may be about 1 to 100, 1 to 10, e.g., about 5 mm$^3$. Herein, by "volume of the tablet", it is meant to refer to the non-expanded state, i.e. prior to exposure to bodily fluids.

The term "oxidized cellulose" (or "OC") refers to a cellulose derivative in which at least some of the primary alcohol groups, e.g., on the carbon 6 of the anhydroglucose unit is oxidized to a carboxylic acid, and is optionally functionalized. OC may include materials, products, articles, or compositions comprising or consisting essentially of OC, e.g., a dressing, fibrin glue, synthetic glue, pad, matrix, powder, tab, pill, suture, fiber, stent, implant, scaffold, solution, gel, wax, gelatin and the like.

OC may be produced by applying an oxidizing agent on cellulose. The oxidizing agent may be selected from, without being limited thereto, chlorine, hydrogen peroxide, peracetic acid, chlorine dioxide, nitrogen dioxide, persulfates, permanganate, dichromate-sulfuric acid, hypochlorous acid, hypohalites, periodates, or any combination thereof, and/or a variety of metal catalysts. Oxidized cellulose may contain carboxylic acid, aldehyde, and/or ketone groups, instead of, or in addition to the original hydroxyl groups of the starting material, cellulose, depending on the nature of the oxidant and reaction conditions.

In exemplary embodiments, OC has been oxidized to contain carboxyl moieties in amounts effective to provide biodegradability. For example, U.S. Pat. No. 3,364,200 discloses the preparation of carboxylic-oxidized cellulose with an oxidizing agent such as dinitrogen tetroxide in a Freon medium. U.S. Pat. No. 5,180,398 discloses the preparation of carboxylic-oxidized cellulose with an oxidizing agent such as nitrogen dioxide in a per-fluorocarbon solvent. After oxidation by either method, the fabric may be thoroughly washed with a solvent such as carbon tetrachloride, followed by aqueous solution of 50 percent isopropyl alcohol (IPA), and finally with 99% IPA. Prior to oxidation, the fabric can be constructed in the desired woven or nonwoven construct.

As used herein with reference to OC, the terms "oxidation level", "degree of oxidation", "carboxyl content", and "carboxylation level" are interchangeable, and may be determined per United States Pharmacopeia (USP) 23-NF18.

Accordingly, in some embodiments, the carboxyl content of the OC is 12 to 24%, by weight. In some embodiments, the carboxyl content of the OC is 12 to 23%, by weight. In some embodiments, the carboxyl content of the OC is 12 to 22%, by weight. In some embodiments, the carboxyl content of the OC is 12 to 21%, by weight.

In some embodiments, the carboxyl content of the OC is 16 to 24%, by weight and the composition can function as a hemostat. In some embodiments, the carboxyl content of the OC is 17 to 23%, by weight. In some embodiments, the carboxyl content of the OC is 18 to 22%, by weight. In some embodiments, the carboxyl content of the OC is 18 to 21%, by weight.

In some embodiments, the carboxyl content of the OC is 12 to 18%, by weight. In some embodiments, the carboxyl content of the OC is 12 to 17%, by weight. In some embodiments, the carboxyl content of the OC is 12 to 16%, by weight.

In some embodiments, the carboxyl content of the OC is 12%, 13%, 14%, 15%, 16%, 17%, 18%, 19%, 20%, 21%, 22%, 23%, or 24%, by weight, including any value and range therebetween.

In certain embodiments of the invention, the OC (e.g., ORC) may be further combined with a hemostatic agent, or other biological or therapeutic compounds, moieties or species, including drugs and pharmaceutical agents. In some embodiments, to improve the hemostatic performance, scaffolds based on the above materials can be combined with biologically-derived clotting factors, such as thrombin and fibrinogen. In yet another embodiment, the disclosed ORC-based composition may be combined with an additive, such as carboxymethyl cellulose (CMC), calcium salt, anti-infective agent, hemostasis promoting agent, gelatin, collagen, saline, or any combination thereof.

In further embodiments of the present invention, the disclosed ORC-based composition may be combined with various additives to further improve the hemostatic properties, wound healing properties, and handling properties. Utilizing additives known to those skilled in the art includes for example: hemostatic additives such as gelatin, collagen, cellulose, chitosan, polysaccharides, starch; biologics-based hemostatic agents as exemplified by thrombin, fibrinogen, and fibrin. Additional biologics hemostatic agents include, without limitation, procoagulant enzymes, proteins, and peptides. Each such agent can be naturally occurring, recombinant, or synthetic, and may be further selected from: fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, albumin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above, and any combination thereof; anti-infective agents, such as chlorhexidine gluconate (CHG), triclosan, silver, and similar anti-bacterial/microbial agents that are known in the art; additives that increase the stickiness of the hemostat; and other additives known in the art.

"Non-woven fabric" refers to a fabric-like material made from long fibers, bonded together by chemical, mechanical, heat or solvent treatment. The term is used in the textile manufacturing industry to denote fabrics, such as felt, which are neither woven nor knitted. Thus, the phrase "non-woven" refers to a sheet, web or mat of directionally or randomly oriented fibers, where fibers are not intercalated but rather bonded through various means, including e.g., friction, cohesion and/or adhesion. The term "non-woven fabric" also includes, but is not limited to, bonded fabrics, formed fabrics, or engineered fabrics, that are manufactured by processes other than spinning, weaving or knitting.

In some embodiments, the tablets further comprise a pharmaceutically acceptable excipient or additive. Excipients and additives may include any pharmaceutically suitable excipient, such as, without being limited thereto, calcium salt, human albumin, mannitol, sodium acetate, sodium chloride, sodium citrate dihydrate, gluconate buffer, saccharose, glycine, sodium acetate, histidine, and polyethylene glycol (PEG).

In an aspect of the present invention, there is provided a method of treating a wound comprising the step of applying (e.g., contacting) the disclosed biodegradable hemostatic tablet in any embodiment thereof onto and/or into the wound of a subject in a need thereof.

By "treating a wound" it further meant to encompass reducing blood loss at a bleeding site of a tissue, e.g., in a patient undergoing surgery. Accordingly, in some embodiments, the method is for reducing blood loss at a bleeding site of a tissue, e.g., in a patient undergoing surgery, comprises contacting the disclosed composition in an embodiment thereof with the bleeding site.

In another aspect of the present disclosure, there is provided a tablet produced by the method of compressing an OC-based material by applying on a surface thereof a pressure indicated herein. In some embodiments, the compression is applied by applying a pressure e.g., using a hydraulic press. In some embodiments, the pressure applied ranges from about 0.2 to about 7 ton/per $cm^2$, including any value and range therebetween.

In some embodiments of the method, the OC material comprises ORC. In some embodiments of this method, the ORC is in the non-woven form. In some embodiments, the method further comprises the step of mixing the OC material with one or more additives selected from, without being limited thereto, calcium salt, anti-infective agent, and hemostasis promoting agent.

The results show that compressed tablets produced from non-woven ORC materials exhibit higher efficacy over prior art compressed forms.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A compressed hemostatic form having a longitudinal axis and a length as measured along the axis comprising:

a) a fibrous non-woven oxidized cellulose (OC) multi-layer material compressed into a form stable tablet, and b) a calcium salt, wherein said tablet rapidly expands along at least the longitudinal axis on contact with liquid blood plasma, wherein (i) said tablet has a tablet length from 3 to 10 mm, and (ii) (ii) said tablet expands, upon contact with blood or blood plasma, from 1.5 to 5 times of said tablet length in 5 seconds; or from 2 to 6 times of said tablet length in 20 seconds; or from 3 to 6 times of said tablet length in 5 minutes, and wherein said form is made by compressing a stack of non-woven OC material in presence of a 10%-20% calcium salt solution in ethanol, followed by drying under vacuum and evaporating said ethanol.

2. The compressed form of claim 1, further comprising a multi-arm polyethylene glycol succinimidyl glutarate (PEG-SG).

3. The compressed form of claim 1, wherein said tablet has a dimensionally stable length as measured along its longitudinal axis for at least 48 hours after compression.

4. The compressed form of claim 1, wherein said tablet has a compression ratio of at least 4 times.

5. The compressed form of claim 1, wherein said tablet has a compression ratio of at least 8 times.

6. The compressed form of claim 1, wherein said tablet has a compression ratio of at least 13 times.

7. The compressed form of claim 2, said tablet is effective in achieving hemostasis as demonstrated in a punch liver or spleen porcine model, using heparinized blood.

8. The compressed form of claim 1, wherein said OC material comprises oxidized regenerated cellulose (ORC).

9. The compressed form of claim 8, wherein said ORC material comprises a compressed form of at least 10 layers of a non-woven fibrous ORC material.

10. The compressed form of claim 1, further comprising a coagulating agent, a clotting factor, an anti-infective agent, or combinations thereof.

11. The compressed form of claim 2, said form made by compressing a stack of non-woven OC material in presence of a 10%-20% calcium salt solution in ethanol, followed by drying under vacuum and evaporating said ethanol, followed by contacting with a solution of the multi-arm PEG-SG in a volatile solvent and vacuum drying.

* * * * *